US009857375B2

(12) United States Patent
Konishi et al.

(10) Patent No.: US 9,857,375 B2
(45) Date of Patent: Jan. 2, 2018

(54) CANCER MARKER AND UTILIZATION THEREOF

(71) Applicant: PUBLIC UNIVERSITY CORPORATION NARA MEDICAL UNIVERSITY, Kashihara-shi, Nara (JP)

(72) Inventors: Noboru Konishi, Kashihara (JP); Keiji Shimada, Kashihara (JP)

(73) Assignee: PUBLIC UNIVERSITY CORPORATION NARA MEDICAL UNIVERSITY, Kashihara-Shi, Nara (JP)

( * ) Notice: Subject to any disclaimer, the term of this patent is extended or adjusted under 35 U.S.C. 154(b) by 0 days.

(21) Appl. No.: 14/436,338

(22) PCT Filed: Sep. 26, 2013

(86) PCT No.: PCT/JP2013/076123
§ 371 (c)(1),
(2) Date: Apr. 16, 2015

(87) PCT Pub. No.: WO2014/061419
PCT Pub. Date: Apr. 24, 2014

(65) Prior Publication Data
US 2015/0260722 A1    Sep. 17, 2015

(30) Foreign Application Priority Data
Oct. 17, 2012   (JP) ................................. 2012-230245

(51) Int. Cl.
G01N 33/574   (2006.01)
A61K 45/06    (2006.01)
A61K 31/713   (2006.01)
C12Q 1/68     (2006.01)

(52) U.S. Cl.
CPC ..... *G01N 33/57488* (2013.01); *A61K 31/713* (2013.01); *A61K 45/06* (2013.01); *C12Q 1/6886* (2013.01); *G01N 33/57407* (2013.01); *G01N 33/57411* (2013.01); *C12Q 2600/118* (2013.01); *C12Q 2600/136* (2013.01); *C12Q 2600/158* (2013.01); *G01N 33/574* (2013.01); *G01N 2333/4703* (2013.01)

(58) Field of Classification Search
CPC ................................................... G01N 33/574
See application file for complete search history.

(56) References Cited

U.S. PATENT DOCUMENTS

| | | | |
|---|---|---|---|
| 2006/0014138 | A1 | 1/2006 | Chinnaiyan et al. |
| 2008/0044839 | A1 | 2/2008 | Chinnaiyan et al. |
| 2009/0233860 | A1 | 9/2009 | Leuschner et al. |
| 2009/0233861 | A1 | 9/2009 | Leuschner et al. |
| 2009/0269341 | A1 | 10/2009 | Leuschner et al. |
| 2010/0009382 | A1 | 1/2010 | Chinnaiyan et al. |
| 2011/0070652 | A1 | 3/2011 | Chinnaiyan et al. |
| 2011/0151490 | A1 | 6/2011 | Hillman et al. |
| 2014/0255513 | A1 | 9/2014 | Leuschner et al. |

FOREIGN PATENT DOCUMENTS

| | | |
|---|---|---|
| EP | 1930445 A1 | 6/2008 |
| JP | 2008502365 | 1/2008 |
| JP | 2011517550 | 6/2011 |
| JP | 2011217749 | 11/2011 |
| JP | 2011528804 | 11/2011 |
| WO | 01/19858 A2 | 3/2001 |
| WO | 2009060835 | 5/2009 |
| WO | 2009121924 | 10/2009 |

OTHER PUBLICATIONS

Deng et al. (Nature. Aug. 21, 2011; 477 (7363): 211-5).*
Têtu (Mod. Pathol. Jun. 2009; 22 (Suppl 2): S53-9).*
Shimada et al. (Diagn. Cytopathol. Jan. 2016; 44 (1): 3-9).*
Massey et al. (J. Alzheimers Dis. Feb. 2004; 6 (1): 79-92).*
Moore et al. (Cancer Res. Oct. 1975; 35 (10): 2684-8).*
Keiji Shimada et al: "Ubiquilin2 as a novel marker for detection of urothelial carcinoma cells in urine", Diagnostic Cytopathology.,vol. 44, No. 1, Aug. 25, 2015, pp. 3-9.
European Search Report for 13847615.5, dated Apr. 25, 2016.
International Preliminary Report on Patentability of PCT/JP2013/076123 dated Apr. 30, 2015.
International Search Report of PCT/JP2013/076123 dated Dec. 3, 2013.
Han-Xiang Deng et al., Mutations in UBQLN2 cause dominant X-linked juvenile and adult-onset ALS and ALS/dementia, Nature (2011) doi:10.1038/nature10353.
Shimada K, Fujii T, Anai S, Fujimoto K, Konishi N., ROS generation via NOX4 and its utility in the cytological diagnosis of urothelial carcinoma of the urinary bladder., BMC Urol. Oct. 28, 2011;11:22.
D. Solomon • R. Nayar Editors, "The Bethesda System for Reporting Cervical Cytology" Springer, p. 1-11.
Sakamoto, A., Rinsho Saibogaku Atorasu [Atlas of Clinical Cytology], Oct. 7, 1993, first edition, first printing.
Byori to Rinsho [Pathology and Clinical Medicine], extra ed., vol. 20, "Saiboshin: Kiso to Oyo" [Basic and Applied Cytodiagnosis], Bunkodo, Mar. 23, 2002.

* cited by examiner

*Primary Examiner* — Stephen Rawlings
(74) *Attorney, Agent, or Firm* — Kristina Castellano; Castellano PLLC

(57) ABSTRACT

The present invention provides a novel cancer marker that is useful in the diagnosis of urothelial cancer. The present invention uses ubiquilin 2 as a cancer marker for urothelial cancer (renal pelvis cancer, ureteral cancer, and bladder cancer). Detection of ubiquilin 2 in a urine sample allows easy and accurate diagnosis of a possibility of urothelial cancer. The present invention is also applicable to the diagnosis of squamous cancer (esophageal cancer, cervical cancer, etc.).

5 Claims, 16 Drawing Sheets

F I G. 4

(a)

|  | NUMBER OF SPECIMENS |
|---|---|
| NEGATIVE (NORMAL) | 100 |
| POSITIVE (CANCER) | 49 |
| TOTAL | 149 |

| POSITIVE (CANCER) | |
|---|---|
|  | NUMBER OF SPECIMENS |
| HIGHLY MALIGNANT | 27 |
| LOW MALIGNANT | 22 |
| TOTAL | 49 |

(b)

| MALIGNANCY | POSITIVE | NEGATIVE | DIFFICULT TO DETERMINE | SENSITIVITY (%) |
|---|---|---|---|---|
| HIGHLY MALIGNANT | 20 | 1 | 6 | 74.1 |
| LOW MALIGNANT | 5 | 7 | 10 | 22.7 |

(c)

| MALIGNANCY | POSITIVE | NEGATIVE | DIFFICULT TO DETERMINE | SENSITIVITY (%) |
|---|---|---|---|---|
| HIGHLY MALIGNANT | 27 | 0 | 0 | 100 |
| LOW MALIGNANT | 19 | 3 | 0 | 86.4 |

(d)

|  | POSITIVE | NEGATIVE | DIFFICULT TO DETERMINE | SPECIFICITY (%) |
|---|---|---|---|---|
| NEGATIVE | 0 | 87 | 13 | 87 |

(e)

|  | POSITIVE | NEGATIVE | DIFFICULT TO DETERMINE | SPECIFICITY (%) |
|---|---|---|---|---|
| NEGATIVE | 0 | 96 | 4 | 96 |

F I G. 9
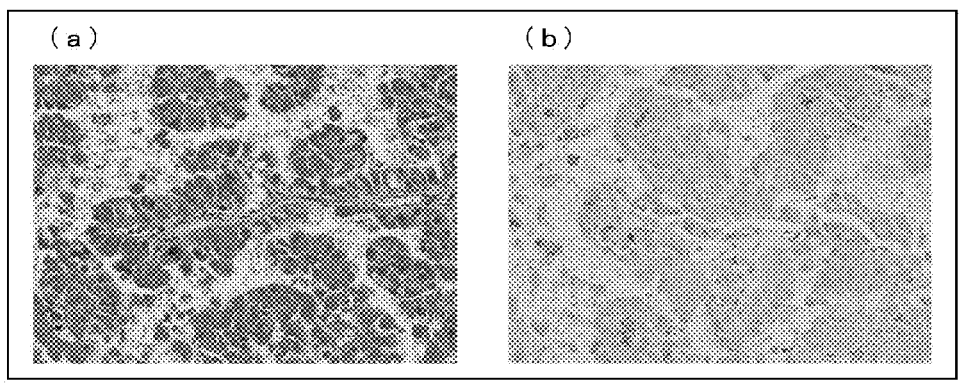

F I G. 1 2
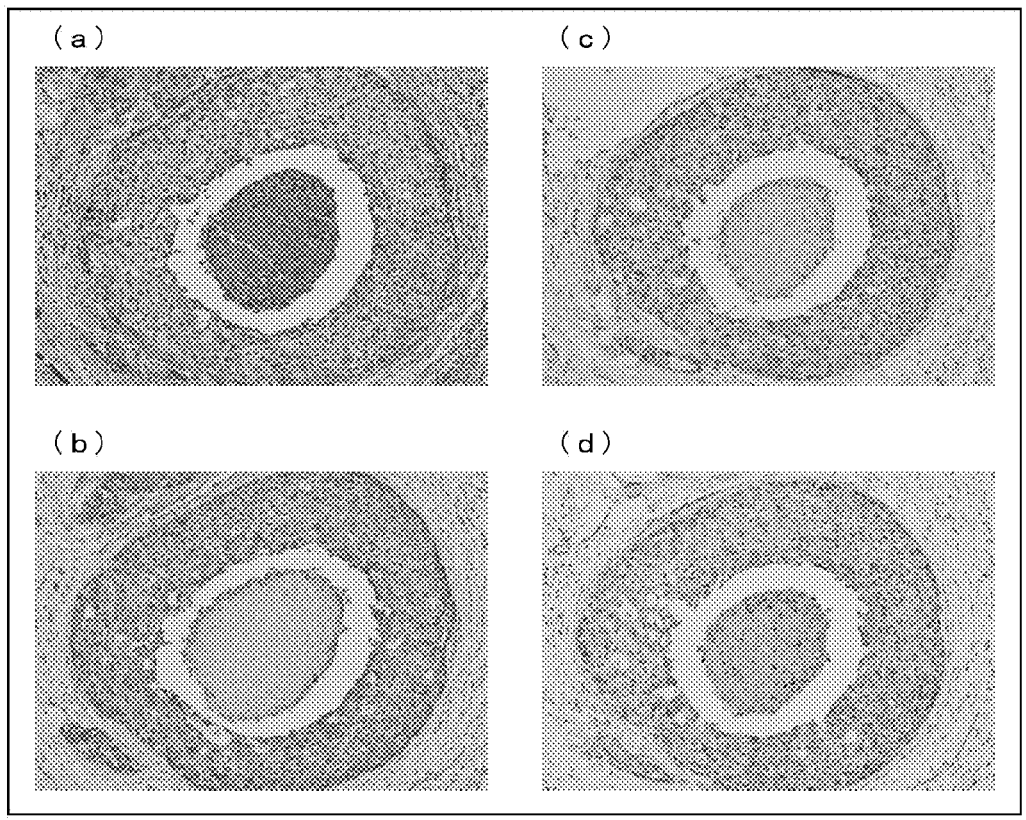

CANCER MARKER AND UTILIZATION THEREOF

CROSS REFERENCE TO RELATED APPLICATIONS

This application is a U.S. National Stage Application of PCT/JP2013/076123 filed on Sep. 26, 2013, which claims priority to Japanese patent application 2012-230245, filed on Oct. 17, 2012, both of which are incorporated herein by reference in their entireties.

TECHNICAL FIELD

The present invention relates to a novel cancer marker that is useful in the diagnosis of urothelial cancer (renal pelvis cancer, ureteral cancer, and bladder cancer) and representative examples of uses thereof. The novel cancer marker according to the present invention is also applicable to the diagnosis (detection) of squamous cancer (esophageal cancer, cervical cancer, etc.).

BACKGROUND ART

The diagnosis of urothelial cancer (renal pelvis cancer, ureteral cancer, and bladder cancer) depends greatly on radiographic diagnostic imaging and histopathological diagnosis of a lesion collected with a ureteroscope or a cystoscope. However, the former, radiographic diagnostic imaging, has difficulty in detection of a non-invasive tumor and has difficulty in differentiating between a calculus or an inflammatory lesion and a cancer, although it is a non-invasive diagnostic method. On the other hand, the latter, histopathological diagnosis, is an invasive diagnostic method in which insertion of an endoscope through the urethra causes devastating agonies to the patient, although the method is high in diagnostic accuracy. Further, since it is necessary to find diseased tissue with the endoscope and collect the diseased tissue, manipulation of the endoscope and determination of the diseased tissue require much skill. Furthermore, even if the endoscope has successfully been inserted into the body, an accurate diagnosis cannot be made unless diseased tissue is finally found.

Under such circumstances, urine cytodiagnosis, which is low in invasiveness, has come to hold an extremely prominent position as a clinical examination method for urothelial cancer (referred to also as "urinary system tumor"). Urine cytodiagnosis is a method of diagnosis through observation of cancer cells appearing in the urine. Various types of cytology, such as urine cytodiagnosis, are disclosed, for example, in Non-patent Literatures 1 to 3.

Urine cytodiagnosis is a so-called non-invasive diagnosis that involves the use as a sample of the urine, which comes naturally out of the body of the patient. As such, urine cytodiagnosis is not painful to the patient. Further, ready availability of a sample makes it possible to perform an examination any number of times. However, urine cytodiagnosis has limitations in a case where the number of cells in a sample is small and in morphological determination of poorly atypical cancer cells, and requires much skill for determination of cancer cells. For this reason, in a case where the number of cells in a sample is small or in a case where the cells are not in a form sufficient to be judged as malignant, there is a risk that a diagnosis of cancer may not be made when it should be made. Further, there are a case where inflammation or the like may cause normal cells to exhibit atypia and a case where responsive tubular epithelial cells in particular may exhibit such atypia as to be taken as cancer. For this reason, there is a risk that non-cancer cells may be diagnosed as cancer cells. Therefore, the existing urine cytodiagnosis is said to be fatally low in diagnostic accuracy (sensitivity), although it is high in specificity (i.e. it has a low probability of diagnosing non-cancer cells as cancer cells). Furthermore, a urine specimen that is used as a sample in urine cytodiagnosis is easily denatured, and depending on handling of the urine specimen, an accurate diagnosis may not be made.

Therefore, there is a demand for the development of a urothelial cancer diagnostic system that is not invasive, i.e. not painful to the patient, and is high in diagnostic accuracy. It should be noted that while cancer markers are considered to be useful in the diagnosis of cancer, no cancer marker has been found yet that is effective in the diagnosis of urothelial cancer.

Through their previous molecular pathological studies of urothelial cancer, the inventors of the present invention found (i) that unlike normal cells, urothelial cancer cells produce an excess of reactive oxygen species (ROS) and (ii) that labelling of ROS allows discrimination of cancer cells from normal cells (see Non-patent Literature 4).

Incidentally, it was revealed that amyotrophic lateral sclerosis (ALS), which causes a gradual decline of muscle strength and finally leads to general anesthesia, is caused by abnormalities in ubiquilin 2 (see Non-patent Literature 5). Ubiquilin 2 has a role in promoting the restoration and utilization of defective or damaged proteins within nerve cells. It is said that when ubiquilin 2 does not function normally, damaged proteins accumulate in nerve cells to severely destroy the nerve cells.

Ubiquilin 2 is a member belonging to the ubiquilin family, and known members other than ubiquilin 2 include ubiquilin 1, ubiquilin 3, and ubiquilin 4. Patent Literatures 1 and 2 teach that ubiquilin 1 can be used as a tumor antigen against prostate cancer, lung cancer, or breast cancer. Further, Patent Literature 3 describes a method for the treatment of tumors, cancers, neoplasms, malignant tumors, and diseases due to proliferation or overproliferation of harmful or abnormal cells, and shows, as an example of its target cell, a cell expressing ubiquilin 1. Further, Patent Literature 4 discloses measuring an expression level of ubiquilin 4 as an index in a method for the detection of a cause of the pathogenesis of colorectal cancer. Further, Patent Literature 5 discloses an anticancer drug containing, as an active ingredient, a small molecule having ubiquilin-binding activity and topoisomerase II inhibitory activity.

CITATION LIST

Patent Literature 1
Japanese Patent Application Publication, Tokukai, No. 2011-217749 A (Publication Date: Nov. 4, 2011)
Patent Literature 2
Japanese Translation of PCT International Application, Tokuhyo, No. 2008-502365 A (Publication Date: Jan. 31, 2008)
Patent Literature 3
Japanese Translation of PCT International Application, Tokuhyo, No. 2011-517550 A (Publication Date: Jun. 16, 2011)
Patent Literature 4
Japanese Translation of PCT International Application, Tokuhyo, No. 2011-528804 A (Publication Date: Nov. 24, 2011)

Patent Literature 5
International Publication No. 2009/060835 Pamphlet (International Publication Date: May 14, 2009)

Non-Patent Literature 1
Byôri to Rinshô [Pathology and Clinical Medicine], extra ed., Vol. 20, "Saibôshin: Kiso to Ôyô" [Basic and Applied Cytodiagnosis], Bunkodo, Mar. 23, 2002.

Non-Patent Literature 2
Sakamoto, A., Rinshô Saibôigaku Atorasu [Atlas of Clinical Cytology], Oct. 7, 1993, first edition, first printing.

Non-Patent Literature 3
Solomon, D. and Nayar, R. ed., translation supervised by Hirai, Y., Besesuda Sisutemu 2001 Atorasu [Bethesda System 2001 Atlas], Springer Japan KK, Nov. 29, 2007.

Non-Patent Literature 4
Shimada, K., Fujii, T., Anai, S., Fujimoto, K., and Konishi, N., ROS generation via NOX4 and its utility in the cytological diagnosis of urothelial carcinoma of the urinary bladder., BMC Urol. 2011 Oct. 28; 11:22.

Non-Patent Literature 5
Han-Xiang Deng et al., Mutations in UBQLN2 cause dominant X-linked juvenile and adult-onset ALS and ALS/dementia, Nature (2011) doi:10.1038/nature10353

SUMMARY OF INVENTION

Technical Problem

As mentioned above, it is most reliable and useful, in diagnosing urothelial cancer, to conduct a histopathological investigation of diseased tissue collected with an endoscope such as a ureteroscope or a cystoscope. However, this causes an absolute pain to and entails a heavy economic burden on the patient.

Meanwhile, urine cytodiagnosis, in which a diagnosis is made through observation of the presence or absence of cancer cells from urinary exfoliated cells, is an inexpensive, simple, and highly-specific examination method, but is fatally low in diagnostic accuracy (sensitivity). In a case where cells with suspected cancer that cannot be judged as cancer cells with certainty are found at urine cytodiagnosis, it is necessary to proceed to the next step of making a histopathological diagnosis with an endoscope. However, an accurate diagnosis cannot be made if cancer tissue is not finally found even by inserting an endoscope into the body, and in the worst case, there may be a case where an organ(s) with suspected cancer must be totally extirpated.

In general, cancer markers are often used in the diagnosis of cancer, but under present circumstances, no cancer marker has been found yet that is effective in the diagnosis of urothelial cancer.

In view of this, the inventors of the present invention examined means effective in the diagnosis of urothelial cancer, and revealed that ROS can be used as a cancer marker for urothelial cancer (see Non-patent Literature 4). However, it was revealed that the method described in Non-patent Literature 4 has several obstacles to overcome toward practical use. Examples of the obstacles are as follows: (a) Labeling of ROS requires living cells that have just been collected. (b) ROS is so unstable that an investigation needs to be conducted in a dark room immediately after labeling. (c) While confirmation of positive cells of ROS requires a fluorescence microscope, morphological attributes are observed with an optical microscope, and this makes it difficult to make a comparative review of results of the confirmation and results of the observation.

Therefore, it can be said that at present there does not exist a urothelial cancer diagnostic system that is not invasive, i.e. not painful to the patient, and high in diagnostic accuracy. In view of this, the present invention has as an object to establish a urothelial cancer diagnostic system that is not invasive, i.e. not painful to the patient, and is high in diagnostic accuracy.

Solution to Problem

In order to attain the foregoing object, the inventors of the present invention searched for a novel cancer marker for urothelial cancer that replaces ROS, and a result of the search, the inventors of the present invention found, surprisingly, that ubiquilin 2, which is a protein that is responsible for the pathogenesis of ALS, exhibits a specifically high level of expression in urothelial cancer cells. The inventors of the present invention constructed a specific antibody to ubiquilin 2 and analyzed the antibody by immunocytological staining and/or flow cytometry. As a result, the inventors of the present invention found (1) that while ubiquilin 2 is not hardly expressed in normal cells, ubiquilin 2 is overexpressed in urothelial cancer cells, mostly in the cytoplasm and nucleus, and (2) that a continuously high level of ubiquilin 2 expression in cancer cells leads to an extremely high level of stability of immunohistological staining, allowing accurate identification of cancer cells. This makes it possible to establish a highly-sensitive and highly-specific non-invasive urothelial cancer diagnostic system that compensates for the aforementioned problems. Further, the inventors of the present invention also found that ubiquilin 2 can also be used as a cancer marker for squamous cancer as well as urothelial cancer.

That is, the present invention encompasses the following inventions:

In order to attain the foregoing object, a kit according to the present invention for detecting urothelial cancer and squamous cancer contains a reagent for detecting ubiquilin 2 in a sample.

Further, in the kit, the reagent may contain a ubiquilin 2 specific antibody.

Further, in the kit, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the kit, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the kit, the urothelial cancer may be one or more members selected from among renal pelvis cancer, ureteral cancer, and bladder cancer, and the squamous cancer may be one or more members selected from among esophageal cancer and cervical cancer.

Meanwhile, in order to attain the foregoing object, a device according to the present invention for automated diagnosis of urothelial cancer and squamous cancer include a ubiquilin 2 detection section for detecting ubiquilin 2 in a sample.

Further, in the device, the ubiquilin 2 detection section may be capable of detecting coloring, luminescence, or fluorescence from a sample treated with a reagent for detecting ubiquilin 2.

Further, in the device, the reagent may contain a ubiquilin 2 specific antibody.

Further, in the device, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the device, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the device, the sample may be a sample obtained from a living organism.

Further, in the device, the urothelial cancer may be one or more members selected from among renal pelvis cancer, ureteral cancer, and bladder cancer, and the squamous cancer may be one or more members selected from among esophageal cancer and cervical cancer.

Meanwhile, a method for obtaining data for diagnosis of urothelial cancer and squamous cancer includes detecting ubiquilin 2 in a sample obtained from a living organism.

The method may further include detecting ubiquilin 2 in the sample with a reagent for detecting ubiquilin 2.

Further, in the method, the reagent may contain a ubiquilin 2 specific antibody.

Further, in the method, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the method, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the method, the sample may be urine.

Further, in the method, the urothelial cancer may be one or more members selected from among renal pelvis cancer, ureteral cancer, and bladder cancer, and the squamous cancer may be one or more members selected from among esophageal cancer and cervical cancer.

Meanwhile, a method according to the present invention for screening an anticancer substance for urothelial cancer and squamous cancer includes: comparing a level of ubiquilin 2 expression in urothelial cancer cells or squamous cancer cells brought into contact with a test article and a level of ubiquilin 2 expression in urothelial cancer cells or squamous cancer cells not brought into contact with a test article; and selecting a test article having an effect of reducing a level of ubiquilin 2 expression.

Meanwhile, an anticancer drug according to the present invention for urothelial cancer and squamous cancer contains a substance that inhibits ubiquilin 2 expression.

Further, in the anticancer drug, the substance may be a ubiquilin 2 gene or siRNA of a partial polynucleotide thereof.

Meanwhile, an anticancer drug additive according to the present invention is an anticancer drug additive, used in combination with an anticancer drug for urothelial cancer and squamous cancer, for enhancing the sensitivity of cancer cells to the anticancer drug, the anticancer drug additive containing a substance that inhibits ubiquilin 2 expression.

Further, in the anticancer drug additive, the substance may be a ubiquilin 2 gene or siRNA of a partial polynucleotide thereof.

Advantageous Effects of Invention

The present invention makes it possible to diagnose urothelial cancer simply by detecting ubiquilin 2 in a urine specimen collected from the patient. Moreover, the present invention allows the diagnosis of urothelial cancer with high diagnostic accuracy and high specificity. Therefore, the present invention makes it possible to provide urothelial cancer diagnostic means that is not invasive, i.e. not painful to the patient, and is high in diagnostic accuracy.

Further, ubiquilin 2 can also be used in the diagnosis of squamous cancer such as esophageal cancer and cervical cancer.

It should be noted that the association between ubiquilin 1 or 4, which is a member other than ubiquilin 2 that belongs to the ubiquilin family, and cancer is known (see Patent Literatures 1 to 5). However, ubiquilin 1 is known as a tumor antigen against prostate cancer, lung cancer, or breast cancer, and ubiquilin 4 is merely known to be usable in the diagnosis of the pathogenesis of colorectal cancer. These types of cancer are totally different from urothelial cancer. No association between ubiquilin 2 and cancer (urothelial cancer in particular) has previously been known at all. Ubiquilin 2 has rather drawn attention as a protein associated with nervous system disease. Given these circumstances, persons skilled in the art cannot predict that ubiquilin 2 can be used as a cancer marker for urothelial cancer. It should be noted that ubiquilin 2 can also be used as a cancer marker for squamous cancer such as esophageal cancer and cervical cancer.

Furthermore, the inventors of the present invention have revealed that suppression of ubiquilin 2 expression can induce apoptosis in urothelial cancer cells and has an effect of enhancing the sensitivity of cancer cells to an endoplasmic reticulum stress agent that is applied to chemotherapy. That is, the inventors of the present invention have revealed that a novel method for the treatment of urothelial cancer and squamous cancer can be provided by targeting ubiquilin 2. These effects are nothing but remarkable and advantageous effects that the present invention brings about.

BRIEF DESCRIPTION OF DRAWINGS

FIG. 4 is a set of tables (a) to (e) showing results of comparison between (i) results of the diagnosis of urothelial cancer on the basis of results of Papanicolaou staining of urinary exfoliated cells (i.e. results of the conventional urine cytodiagnosis) and (ii) results of the diagnosis of urothelial cancer on the basis of results of immunocytological staining of urinary exfoliated cells with a ubiquilin 2 specific antibody (i.e. results of the urine cytodiagnosis according to the present invention), the table (a) showing a breakdown of the subjects, the table (b) showing results of the conventional urine cytodiagnosis of positive (cancer) urine specimens, the table (c) showing results of the urine cytodiagnosis according to the present invention of positive (cancer) urine specimens, the table (d) showing results of the conventional urine cytodiagnosis of negative (normal) urine specimens, the table (e) showing results of the urine cytodiagnosis according to the present invention of negative (normal) urine specimens.

FIG. 9 is a set of photographs (a) and (b), the photograph (a) showing a result of HE staining of diseased tissue of renal cancer, the photograph (b) showing a result of immunostaining of diseased tissue of renal cancer with a ubiquilin 2 specific antibody.

FIG. 12 is a set of photographs (a) to (d) showing a result of HE staining of diseased tissue of breast cancer and results of immunostaining of the diseased tissue with a ubiquilin 1, 2, or 4 specific antibody, respectively, the photograph (a) showing a result of HE staining, the photograph (b) showing a result of immunostaining of diseased tissue with a ubiquilin 2 specific antibody, the photograph (c) showing a result of immunostaining of diseased tissue with a ubiquilin 1 specific antibody, the photograph (d) showing a result of immunostaining of diseased tissue with a ubiquilin 4 specific antibody.

DESCRIPTION OF EMBODIMENTS

Figure 1:
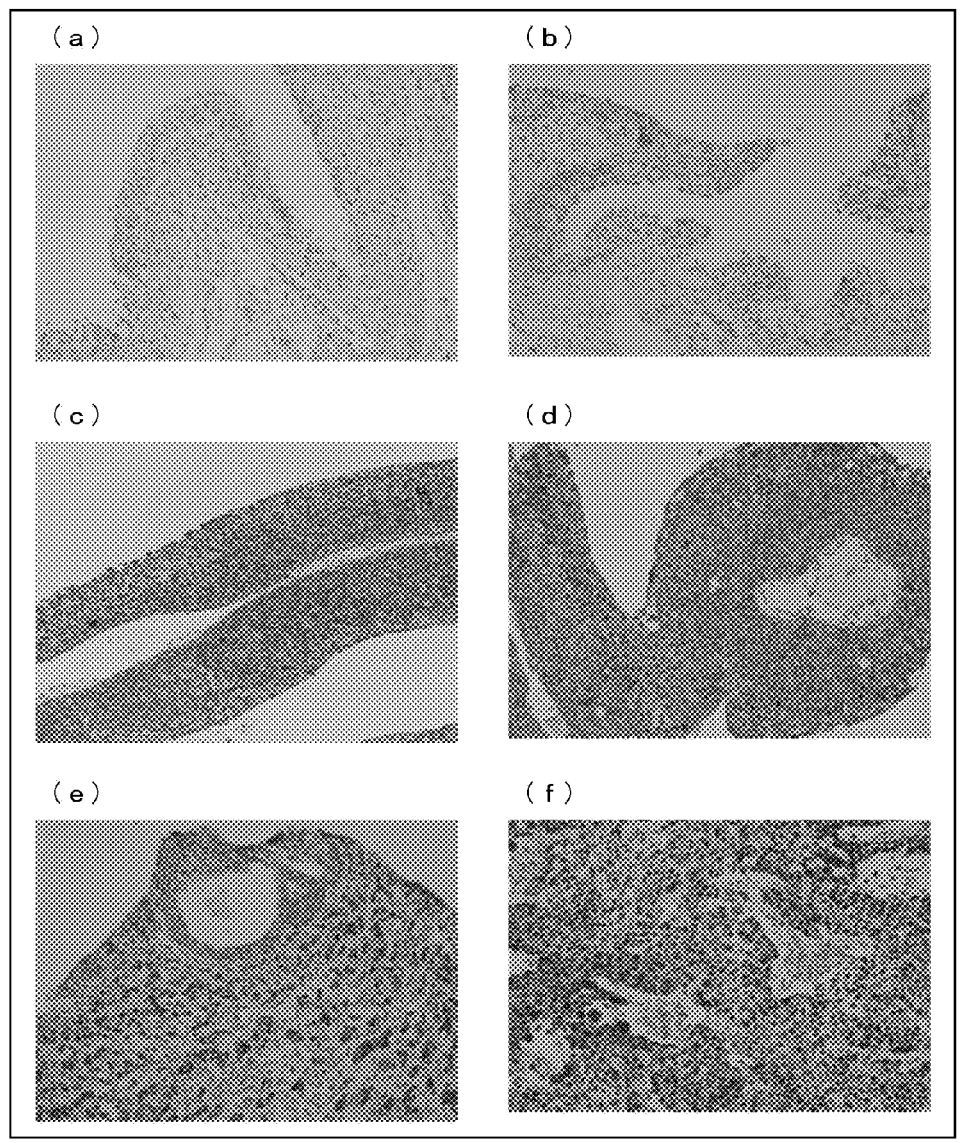
FIG. 1 is a set of photographs (a) to (f) showing results of immunohistological staining with a ubiquilin 2 specific antibody, the photographs (a) and (b) showing results of immunohistological staining of normal urothelia, the photographs (c) and (d) showing results of immunohistological staining of non-invasive urothelial cancer (low malignant), the photographs (e) and (f) showing results of immunohistological staining of invasive urothelial cancer (highly malignant).

In the following, the present invention is described in detail. However, the scope of the present invention should not be bound by these descriptions, and variations other than those illustrated below may be carried out appropriately within the limits of the spirit of the present invention. Further, all of the publicly-known documents described herein are incorporated herein by reference.

As used herein, the term "polypeptide" is used interchangeably with "peptide" or "protein". A polypeptide may be one isolated from a natural supply source, one engineered recombinantly, or one synthesized chemically. Further, as used herein, the term "polynucleotide" is used interchangeably with "gene", "nucleic acid", or "nucleic acid molecule", and is intended to mean a nucleotide polymer. Further, the term "gene" is meant to encompass RNA (e.g. mRNA) as well as DNA. As used herein, the term "base sequence" is used interchangeably with "gene sequence", "nucleic acid sequence", or "nucleotide sequence", and is represented as a sequence of deoxyribonucleotide (which is abbreviated as A, G, C, and T).

1. Detection of Urothelial Cancer and Squamous Cancer with Ubiquilin 2

As a result of their unique study, the inventors of the present invention found that ubiquilin 2 exhibits a specifically high level of expression in diseased tissue of urothelial cancer (renal pelvis cancer, ureteral cancer, and bladder cancer) and squamous cancer (esophageal cancer, cervical cancer, etc.). Moreover, the inventors of the present invention have first revealed that ubiquilin 2 can be used as a cancer marker (which is referred to also as "tumor marker") for urothelial cancer and squamous cancer. That is, the gist of the present invention is to use ubiquilin 2 as a cancer marker for urothelial cancer and squamous cancer.

Ubiquilin 2 is known as a ubiquitin-associated protein, and belongs to the ubiquilin family (ubiquilin 1-4). It has recently been revealed that ubiquilin 2 is a protein that is responsible for the pathogenesis of ALS (see Non-patent Literature 5). Ubiquilin 2 has its gene cloned, and the base sequence of cDNA (mRNA) thereof is registered by Accession Number: BC069237.1 in the gene database GenBank. The amino acid sequence of ubiquilin 2 is represented by SEQ ID NO. 1, and the base sequence of cDNA of the ubiquilin 2 gene is represented by SEQ ID NO. 2.

The amino acid sequence of ubiquilin 2 is not limited to that of SEQ ID NO. 1, and may encompass a variant thereof. That is, the origin of the ubiquilin 2 gene encoding ubiquilin 2 and a variant protein than can be produced by mutation are also encompassed in ubiquilin 2 in the description of the present invention. In other words, a variant protein having an amino acid sequence with a substitution, deletion, insertion, and/or addition of one or several amino acids in the amino acid sequence of SEQ ID NO: 1 and having ubiquilin 2 activity (i.e. the activity to promote the restoration and utilization of defective or damaged proteins within nerve cells) is also encompassed in ubiquilin 2 in the description of the present invention. The phrase "with a substitution, deletion, insertion, and/or addition of one or several amino acids" is not particularly limited, but means a substitution, deletion, insertion, and/or addition of such a number of amino acids (preferably 10 or less, more preferably 7 or less, even more preferably 5 or less) that can be substituted, deleted, inserted, and/or added by a publicly-known method for the construction of a variant protein, such as site-directed mutagenesis.

The present invention makes it possible to, by detecting ubiquilin 2 expression in a sample (such as urine, saliva, phlegm, blood, cell, tissue) obtained from a living organism, evaluate (diagnose) the sample (or the living organism from which the sample was obtained) for (with) the high possibility of cancer.

The sample obtained from a living organism (which is referred to as "biological sample") is not particularly limited, but may be a biological sample obtained non-invasively (i.e. a sample collectable without damage to a living organism such as a patient; referred to also as "non-invasively-obtained biological sample") or may be a biological sample obtained invasively (i.e. a sample that is collected with damage to a living organism such as a patient; referred to also as "invasively-obtained biological sample"). Examples of non-invasively-obtained biological samples include urine, blood (serum, plasma), body fluid, lymph fluid, digestive secretion, etc. Further, examples of invasively-obtained biological samples include diseased tissue obtained with an endoscope or surgery. However, in view of a burden on the patient, it is preferable that the sample obtained from a living organism be a non-invasively-obtained biological sample such as urine.

It should be noted that the origin of a biological sample in the description of the present invention is not particularly limited to a human, as long as it is a living organism that may develop urothelial cancer or squamous cancer, and examples of such living organisms include mammals in general, such as dogs, cats, sheep, goats, mice, rats, rabbits, cows, horses, and pigs.

It should be noted here that examples of biological samples for detection of urothelial cancer include diseased tissue obtained invasively with an endoscope or the like from the bladder, the ureter, or the renal pelvis and non-invasively-obtained biological samples of urine. Since urine contains an exfoliated cell (urinary exfoliated cell), detection of ubiquilin 2 for this cell allows the diagnosis of urothelial cancer.

Meanwhile, squamous cancer is a cancer that is found in the esophagus, the mouth, the tongue, the pharynx, the vocal chord, the trachea, the bronchi, the larynx, the anus, the vulva, the vagina, the cervix uteri, the portio vaginalis uteri, or the like. For some types of squamous cancer, such as esophageal cancer, phlegm or saliva obtained non-invasively can be used as a biological sample, but basically, diseased tissue obtained invasively may be used as a biological sample.

A method for the detection of ubiquilin 2 in a biological sample is not particularly limited, and can be carried out appropriately with a publicly-known method. An example is a method for detection with a ubiquilin 2 specific antibody (which is an antibody capable of binding specifically to ubiquilin 2). The ubiquilin 2 specific antibody may be a polyclonal antibody or a monoclonal antibody. Further, the ubiquilin 2 specific antibody may be an antibody fragment such as an Fab and F(ab')$_2$ fragment, as well as a complete antibody molecule. An Fab and F(ab')$_2$ fragment can be suitably used, as it lacks the Fc portion of a complete antibody, is further quickly removed by circulation, and can hardly have the non-specific binding of a complete antibody (Wahl et al., *J. Nucl. Med.* 24:316-325 (1983)).

It should be noted that the ubiquilin 2 specific antibody may be a commercially-available or self-made one. A commercially-available ubiquilin 2 specific antibody can be purchased, for example, from Santa Cruz Biotechnology, Inc. (United States).

The ubiquilin 2 specific antibody may be one constructed, for example, by a conventionally publicly-known method using the full length of or a partial fragment of ubiquilin 2 as an antigen. The partial fragment of ubiquilin 2 (referred to also as "partial polypeptide of ubiquilin 2") needs only be one which has immunogenicity and from which the ubiquilin 2 specific antibody can be induced. The number of peptides of the partial fragment of ubiquilin 2 is not particularly limited, but is preferably seven or more amino acids or more preferably ten or more amino acids.

A method for the production of a ubiquilin 2 specific antibody (monoclonal antibody) is not particularly limited; for example, such a monoclonal antibody needs only be obtained from antibody-producing hybridomas produced by fusion of spleen lymphocytes of a mouse immunized with an antigen and mouse-derived myeloma cells. Usable examples of methods for the production of hybridomas include, but are not particularly limited to, conventionally publicly-known methods such as the hybridoma technique (Kohler, G. and Milstein, C., *Nature* 256, 495-497 (1975)), the trioma technique, the human B-cell hybridoma technique (Kozbor, *Immunology Today* 4, 72(1983)), and the EBV-hybridoma technique (*Monoclonal Antibodies and Cancer Therapy*, Alan R Liss, Inc., 77-96 (1985)).

Further, the antigen is not particularly limited provided it is a polypeptide, but may be an antigen protein produced by binding a substance serving as an antigen determinant to a carrier protein. Specifically, when the antigen is a hapten, it cannot produce an antibody, as it does not have the capability of inducing antibody production or the like; however, antibody production can be induced by immunization with an antigen protein produced by a covalent bond of the antigen to a carrier consisting of biopolymers such as heterologous proteins. Suitably usable examples of the carrier include, but are not particularly limited to, various types of protein that have conventionally been publicly known in this technical field, such as ovalbumin, gamma globulin, and hemocyanin. Further, a monoclonal antibody can also be produced by gene recombination technology or the like.

Further, a possible example of a method for the production of a ubiquilin 2 specific antibody (polyclonal antibody) is a method for obtaining such a polyclonal antibody through purification of an antibody component from a body fluid of a laboratory animal inoculated and sensitized with an antigen (ubiquilin 2 or a partial fragment thereof). Examples of animals to be immunized include, but are not particularly limited to, conventionally publicly-known laboratory animals such as mice, rats, rabbits, monkeys, and horses. In the case of inoculation and sensitization of an antigen, the intervals of inoculation of the antigen and the amount of intake of the antigen can be set as appropriate according to the usual methods.

Further, detection of ubiquilin 2 in a biological sample with a ubiquilin 2 specific antibody can be carried out with a publicly-known immunoassay. Possible examples of the immunoassay include publicly-known immunoassays such as flow cytometry, RIA, ELISA (solid-enzyme immunoassay), and fluorescent antibody technique. Besides those named above, the following methods can be used as needed: Western blotting; an enzyme immunoassay; a method of observation of antibody-mediated agglutination, sedimentation, and/or hemolysis; an antibody array technique; and morphological detection methods such as tissue immunostaining and cell immunostaining.

Of the assays named above, ELISA is preferred because of its high sensitivity and simplicity. For example, ELISA is a technique for measuring a protein concentration of ubiquilin 2 with a ubiquilin 2 specific antibody after immobilizing proteins contained in a biological sample onto a multi-well plate (referred to also as "microtiter plate"). For example, a ubiquilin 2 specific antibody bonded to ubiquilin 2 may be detected by using an alkaline phosphatase or peroxidase-labeled anti-IgG antibody as a secondary antibody. ELISA may be the sandwich technique.

On the other hand, Western blotting is a technique for measuring a protein concentration of ubiquilin 2 with a ubiquilin 2 specific antibody, in which technique a biological sample is separated by SDS-polyacrylamide electrophoresis and then transferred to a nitrocellulose sheet. A ubiquilin 2 specific antibody bonded to ubiquilin 2 may be detected, for example, by using $^{125}$I-labeled protein A, a peroxidase-labeled anti-IgG antibody, or the like as a secondary antibody. A protein concentration of ubiquilin 2 can be measured, for example, by confirming a signal intensity obtained by using a densitometer or the like. That is, it is judged that a higher signal intensity indicates a higher protein concentration of ubiquilin 2. Further, a calibration curve is created as needed, and by using this calibration curve, the concentration of ubiquilin 2 in the biological sample can be measured.

Since ubiquilin 2 is a protein that exhibits a specifically high level of expression in urothelial cancer or squamous cancer, it is possible, in the present invention, to judge (diagnose) that detection of ubiquilin 2 in a biological sample thus measured indicates a possibility of the presence of urothelial cancer or squamous cancer in the biological sample. Further, it is also possible to measure and compare the protein concentration of ubiquilin 2 in a biological sample derived from a subject being tested and the protein concentration of ubiquilin 2 in a biological sample derived from a healthy subject and, in a case where the former is significantly higher, judge that there is a possibility of the presence of urothelial cancer or squamous cancer. The protein concentration of ubiquilin 2 in a biological sample derived from a healthy subject may be measured every time. Alternatively, the protein concentration of ubiquilin 2 in a biological sample derived from a healthy subject may be measured in advance to be used for comparison with the protein concentration of ubiquilin 2 in a biological sample derived from a subject being tested, and in a case where the latter is significantly higher, it may be judged that there is a possibility of the presence of urothelial cancer or squamous cancer. Furthermore, the presence or absence of urothelial cancer or squamous cancer in a biological sample derived from a subject being tested may be determined according to whether the concentration of ubiquilin 2 in the biological sample is higher than a preset boundary value (cutoff value) that allows determination of the presence or absence of urothelial cancer or squamous cancer in a biological sample. The boundary value is not limited, as it can vary depending on the biological sample being used or the type of cancer. However, a person skilled in the art who has viewed the descriptions in the present specification can set the boundary value without the need for undue trial and error.

Detection of ubiquilin 2 in a biological sample in the present invention can be performed through detection of a genetic level as well as the detection of a protein level. That is, detection of ubiquilin 2 in the present invention may be such an aspect that the level of ubiquilin 2 protein expression is measured by measuring the amount of mRNA in the ubiquilin 2 gene. Since ubiquilin 2 is a protein that exhibits a specifically high level of expression in urothelial cancer or squamous cancer, a possibility of the presence of urothelial cancer or squamous cancer in a biological sample can be determined simply by detecting the mRNA of the ubiquilin 2 gene in a sample derived from a living organism. Further, it is also possible, in the present invention, to measure and compare the amount of mRNA of the ubiquilin 2 gene in a biological sample derived from a subject being tested and the amount of mRNA of the ubiquilin 2 gene in a biological sample derived from a healthy subject. Then, in a case where the former exhibits a higher level of expression, it can be judged that there is a possibility of the presence of urothelial cancer or squamous cancer in the biological sample derived from the subject being tested.

The amount of mRNA in the ubiquilin 2 gene in a biological sample derived from a healthy subject may be measured every time; however, the amount of mRNA in the ubiquilin 2 gene in a biological sample derived from a healthy subject may be measured in advance for use. Furthermore, the presence or absence of digestive system cancer in a sample derived from a subject being tested may be determined according to whether the amount of mRNA in the biological sampled derived from the subject being tested is higher than a preset boundary value (cutoff value) that allows determination of the presence or absence of urothelial cancer or squamous cancer in a subject being tested.

A method for the measurement of an amount of mRNA is not particularly limited provided it allows measurement of a desired amount of mRNA, but can be appropriately selected from among publicly-known methods for use. An example of the method is one that involves the use of a primer or probe containing a polynucleotide which consists of a part of the mRNA of a ubiquilin 2 gene, the cDNA thereof, or a complementary strand thereof and which binds (hybridizes) site-specifically to (with) the RNA or cDNA of the ubiquilin 2 gene.

Specifically, the mRNA or cDNA can be detected by labeling the primer or probe and detecting the label. Then, the amount of mRNA can be measured by examining the signal strength of the label. Examples of the label include, but are not particularly limited to, a fluorescent substance such as fluorescein as well as a radioactive substance such as $^{32}P$. The polynucleotide to be used as the primer and/or probe may be designed by a conventionally publicly-known method on the basis of the base sequence of the ubiquilin 2 gene of SEQ ID NO. 2. For example, a probe can be constructed by constructing a DNA probe of an appropriate length as a DNA probe from the base sequence of the ubiquilin 2 gene and appropriately labeling the DNA probe with a fluorescent label or the like. Further, as the probe, a probe for use in detection consisting of a full-length or partial sequence of the antisense strand of the ubiquilin 2 gene may be employed. Since it is well known to persons skilled in the art that a polynucleotide that is utilizable as a primer to specifically amplify the target mRNA (cDNA) is usable as a probe to specifically detect the mRNA (cDNA), it is also possible to design, on the basis of this finding, a polynucleotide that is utilizable as a probe.

In the construction of the probe, an example of conditions for hybridization with the ubiquilin 2 gene under stringent conditions is hybridization at 42° C. and washing treatment at 42° C. with a buffer solution containing 1×SSC (0.15 M NaCl, 0.015 M sodium citrate) and 0.1% SDS (sodium dodecyl sulfate), more preferably hybridization at 65° C. and washing treatment at 65° C. with a buffer solution containing 0.1×SSC and 0.1% SDS. There are various factors other than the temperature conditions that affect the stringency of hybridization, and a person skilled in the art would be able to combine any of the various factors to achieve the same level of stringency as the stringency of hybridization illustrated above. Further, the "stringent conditions" can be said to be conditions under which hybridization occurs only in the presence of an identity of at least 90% or higher, preferably at least 95% or higher, most preferably 97%, between sequences.

Examples of publicly-known methods for the detection of mRNA with a primer or probe containing a polynucleotide that binds site-specifically to mRNA or cDNA include RT-PCR, real-time RT-PCR, competitive PCR, in-situ hybridization, in-situ PCR, a DNA array technique, Northern blotting, etc.

RT-PCR (reverse transcriptase polymerase chain reaction) is a technique for amplifying DNA through PCR after synthesizing cDNA through reverse transcriptase reaction with use of the mRNA of the ubiquilin 2 gene as a template (Reference: Kawasaki, E. S. et al., *Amplification of RNA. In PCR Protocol, A Guide to methods AND applications*, Academic Press, Inc., San Diego, 21-27 (1991)). DNA amplification reaction is not particularly limited, and a person skilled in the art can consider and adopt optimum conditions as appropriate. Further, an amplification region of the ubiquilin 2 gene does not necessarily need to be a full-length region, and may be a partial region of the gene provided it does not pose a problem for the confirmation of an amplification product. The amount of amplified DNA (which corresponds to the amount of mRNA) can be detected, for example, by using a probe that hybridizes specifically with the target amplification fragment after subjecting the DNA amplification reaction solution to agarose gel electrophoresis. Meanwhile, in a case where a sufficient amount of amplification product can be obtained, it is also possible to confirm the amount of amplified DNA by the position and fluorescence intensity of an amplified polynucleotide through EtBr staining of gel after agarose gel electrophoresis.

Furthermore, during RT-PCT, real-time RT-PCR can be performed by using a real-time monitoring reagent. Real-time RT-PCR is a technique for monitoring and analyzing a process of creation of an amplification product in real time. This makes it possible to stop the amplification reaction before saturation of the amount of amplification of the amplification product. This makes it possible to more accurately measure the amount of mRNA in the ubiquilin 2 gene. Examples of the real-time monitoring reagents include SYBR (registered trademark: Molecular Probes, Inc.) Green, a TaqMan (registered trademark: Applied Biosystems, Inc.) probe, etc.

In performing RT-PCR, a primer pair consisting of a sense primer and an antisense primer for the amplification of the ubiquilin 2 gene is used.

Further, detection of ubiquilin 2 in the present invention can also be simply performed with an Invader (registered trademark) assay. For example, it can be performed by designing a signal probe having a base sequence and an enzyme cleavage site that hybridize specifically with the ubiquilin 2 gene and bringing the signal probe into reaction with total RNA (which may be cDNA) extracted from a biological sample, Invader (registered trademark) Oligo, Cleavase (registered trademark) Enzyme, and a FRET Probe at a predetermined temperature and for a predetermined period of time (e.g. at 63° C. for 2 hours). For specific experiment techniques and conditions, refer to the following references: (i) T. J. Griffin et al., *Proc Natl Acad Sci USA* 96, 6301-6 (1999); (ii) M. W. Kaiser et al., *J Biol Chem* 274, 21387-94 (1999); (iii) V. Lyamichev et al., *Nat Biotechnol* 17, 292-6 (1999), (iv) R. W. Kwiatkowski et al., *Mol Diagn* 4, 353-64 (1999), (v) J. G. Hall et al., *Proc Natl Acad Sci USA* 97, 8272-7 (2000), (vi) M. Nagano et al., *J Lipid Res* 43, 1011-8 (2002), etc. As described above, use of the Invader assay allows quick and low-cost detection of ubiquilin 2, as it sometimes avoids the need for gene amplification. It should be noted that use of a commercially-available Invader assay kit makes it possible to more easily carry out the present invention.

Further, the amount of mRNA in the ubiquilin 2 gene may also be measured by Northern hybridization. In this case, the amount of mRNA can be measured by extracting a certain amount of crude RNA sample from a biological sample, fractioning the sample according to the molecular weight and the like, immobilizing the sample onto a nylon filter or the like, bringing an object to be detected, i.e. the mRNA of the ubiquilin 2 gene, and a probe into contact with each other, and detecting the probe having hybridized with the mRNA.

Further, measurement of the amount of mRNA in the ubiquilin 2 gene by in-situ hybridization can be performed in the following manner, e.g. can be easily performed by labeling the ubiquilin 2 gene or a partial sequence thereof, using it as a probe for detection, forming a molecular hybrid directly in a specimen of biological sample on a glass slide, and detecting the part where the molecular hybrid has been formed. Specifically, a thin section (such as a paraffin section or a frozen section) of a biological sample is prepared on a glass slide and labeled with a probe for detection, and the probe for detection is hybridized, and is then washed away in a similar manner to Northern hybridization, followed by application and exposure of photographic emulsion. After development, the location of hybridization is identified from a distribution of silver particles. For more specific experiment techniques and conditions, refer to the following references: (i) "*Inshitsu Haiburidaizêshon Hou*" [In-situ Hybridization], (July 1995), Furusho, T. and Imura, H. ed., Kanehara 86 Co., Ltd., p. 932-937; and (ii) "Inshitsu Haiburidaizêshon-ni yoru Idenshihatsugen no Kaiseki" [Analysis of Gene Expression by In-situ Hybridization], "*Idenshi Kôgaku Jikken*" [Genetic Engineering Experiments], (May 1991), Nomura, S., Japan Radioisotope Association, p. 221-232. There are two types of in-situ hybridization, namely a method in which DNA labelled with a radio isotope (mainly $^3$H) is used as a probe for detection to detect its locus by autoradiography and a method in which a fluorescence signal from a labeled probe for detection is detected under a fluorescence microscope. Either of the methods may be used.

Further, measurement of the amount of mRNA in the ubiquilin 2 gene by the DNA array technique can be performed in the following manner. The cDNA of the ubiquilin 2 gene or a partial sequence thereof is immobilized on a support, and is hybridized with mRNA or cDNA prepared from a biological sample. In so doing, fluorescent labeling or the like of the mRNA or cDNA allows detection of hybridization between the cDNA or the partial sequence thereof immobilized on the support and the RNA or cDNA prepared from the sample.

The amount of mRNA can be measured, for example, by confirming a signal intensity obtained by using a densitometer or the like with respect to the mRNA or cDNA detected by the aforementioned method. That is, it is judged that a higher signal intensity indicates a larger amount of mRNA or cDNA.

As the DNA array, any publicly-known conventional type of microarray can be suitably used, such as a DNA microarray from United States Affymetrix Inc., a Stanford type of DNA microarray, or a DNA microarray in which an oligonucleotide is chemically synthesized directly on a silica substrate with a microfabrication technology that is used in semiconductor manufacturing. The DNA array is not particularly limited in its specific size, shape, system, etc. The DNA microarray for detection of ubiquilin 2 is used to carry out the present invention, and is encompassed in the intended scope of the present invention.

As mentioned above, the gist of the present invention is to use ubiquilin 2 as a cancer marker for urothelial cancer and squamous cancer to be able to detect (diagnose) urothelial cancer and squamous cancer. Examples of the urothelial cancer include renal pelvis cancer, ureteral cancer, and bladder cancer, and examples of squamous cancer include cervical cancer, esophageal cancer, skin cancer, and tongue cancer.

Moreover, the present invention encompasses an invention directed a kit for detecting urothelial cancer and squamous cancer (hereinafter referred to as "detection kit of the present invention"). The detection kit of the present invention contains a reagent for detecting ubiquilin 2 in a sample. An example of the "sample" here is the "biological sample" explicated above. It should be noted that an explanation of the biological sample has already been given.

Further, although the "reagent for detecting ubiquilin 2 in a sample (hereinafter referred to a "detection reagent") is intended to mean all articles that are capable of detecting ubiquilin 2 in a sample, examples of the detection reagent can include the "ubiquilin 2 specific antibody" explicated above. Inclusion of the ubiquilin 2 specific antibody in the detection reagent allows detection of ubiquilin 2 in a sample at a protein level. An example of the ubiquilin 2 specific antibody is, but is not particularly limited to, an antibody that is induced with a polypeptide of (1) or (2) and that binds specifically to the polypeptide:

(1) a polypeptide consisting of the amino acid sequence of SEQ ID NO. 1; and (2) a partial polypeptide of the polypeptide (1).

It should be noted that an explanation of the ubiquilin 2 specific antibody has already been given. The term "partial polypeptide of the polypeptide (1)" means a partial fragment, excluding the full-length of the polypeptide of (1).

Further, an example of the detection reagent is a polynucleotide that hybridizes under stringent conditions with a polynucleotide of any of (3) to (5):

(3) a polynucleotide consisting of the base sequence of SEQ ID NO. 2;

(4) an antisense strand of the polynucleotide consisting of the base sequence of SEQ ID NO. 2; and (5) a polynucleotide consisting of a partial base sequence of the polynucleotide (3) or (4).

Ubiquilin 2 in a sample can be detected at a genetic level by using any of these polynucleotides, for example, as a probe. The detection of ubiquilin 2 at a genetic level has already been described.

The term "polynucleotide consisting of a partial base sequence of the polynucleotide (3) or (4)" means some polynucleotide ("partial polynucleotide"), excluding the full-length of the polynucleotide (3) or (4). It should be noted that the partial polynucleotide is not particularly limited in length provided it has such a length that a probe can hybridize with the partial polynucleotide.

The detection kit of the present invention may include all reagents (e.g. a secondary antibody, a coloring reagent, a blocking reagent, a buffer solution such as a phosphate buffer solution, a DNA polymerase, etc.) and instruments (such as a microtiter plate, a microtube, a DNA microarray, an antibody array, a thermal cycler, and a fluorescence microscope) that are used for detecting ubiquilin 2 in a sample. Further, the detection kit of the present invention may also include a manual (instructions manual) on a method, reagent, apparatus, etc. for the detection of ubiquilin 2.

Further, the present invention also encompasses an invention directed to a device for automated diagnosis of urothelial cancer and squamous cancer (hereinafter referred to as "automated diagnostic device of the present invention"). Moreover, the automated diagnostic device of the present invention includes at least a "ubiquilin 2 detection section for detecting ubiquilin 2 in a sample".

The ubiquilin 2 detection section is not particularly limited provided it is configured to automatically detect ubiquilin 2 in a sample. For example, the ubiquilin 2 detection section may be configured to be able to detect luminescence or fluorescence from a sample treated with a reagent for detecting ubiquilin 2 (e.g. a ubiquilin 2 specific antibody or the like). It should be noted that the reagent for detecting ubiquilin 2 has already been described.

The principle of detection of ubiquilin 2 by the automated diagnostic device of the present invention can be embodied, for example, with ELSA, flow cytometry, etc. For example, in a case where urine is used as a biological sample and ubiquilin 2 in urinary exfoliated cells is detected, a sample obtained by bringing urine into contact with the ubiquilin 2 specific antibody, bringing it into contact with the secondary antibody, and then coloring it with the coloring reagent is applied to the automated diagnostic device of the present invention. The automated diagnostic device of the present invention is provided with an absorptiometer as the ubiquilin 2 detection section so that ubiquilin 2 in the sample of urine can be detected on the basis of the principle of ELISA. Further, the automated diagnostic device of the present invention is provided with a flow cytometer as the ubiquilin 2 detection section so that ubiquilin 2 in the sample of urine can be detected on the basis of the principle of flow cytometry.

The automated diagnostic device of the present invention may be configured, as described above, such that only detection is automatically performed after treatment of a reagent for detecting ubiquilin 2 and a biological sample has been manually performed, but may instead be configured such that all operations including treatment of a reagent for detecting ubiquilin 2 and a biological sample are automatically performed. In this case, the automated diagnostic device of the present invention includes a "sample treatment section" for automatically performing the treatment of a biological sample with a ubiquilin 2 detection reagent. Provision of the sample treatment section makes it possible to obtain data for diagnosis simply by putting a sample into the automated diagnostic device of the present invention, thus allowing easier and high-throughput diagnosis.

Further, the automated diagnostic device of the present invention may include: a "data processing section" for calculating the concentration of ubiquilin 2 from the data (e.g. coloring intensity, fluorescence intensity, etc.) obtained by the ubiquilin 2 detection section, and/or for comparing the data obtained by the ubiquilin 2 detection section with data from a healthy subject; and/or a "data determination section" for judging (diagnosing) a possibility of cancer from a cutoff value inputted in advance. Provision of these components in the automated diagnostic device of the present invention makes it possible to automatically diagnose cancer simply by putting a sample into the automated diagnostic device of the present invention, thus allowing much easier and high-throughput diagnosis.

Further, the automated diagnostic device of the present invention may include a "data storage section" in which diagnostic data on various types of specimen is stored. Provision of this component in the automated diagnostic device of the present invention makes it possible to monitor patients over time and/or make comparisons with previous cases.

Furthermore, the automated diagnostic device of the present invention may include a "network processing section" that allows information exchange of diagnostic data between terminals via various types of network. Provision of this component in the automated diagnostic device of the present invention brings about merits such as allowing a doctor who is in a remote location from a patient to know diagnostic outcome, allowing easy sharing of data between doctors in attendance, and allowing easy and accurate cooperation with a hospital to which the patient has been transferred.

Although the detection kit and automated diagnostic device of the present invention allow diagnosis of urothelial cancer or squamous cancer, the present invention even encompasses a method for obtaining data for diagnosis of urothelial cancer and squamous cancer, the method including detecting ubiquilin 2 in a sample obtained from a living organism. It should be noted that the method of the present invention for obtaining data corresponds to a method for the treatment of a sample collected from a living organism such as a human (such as blood, urine, skin, hair, cells, or tissue) or to a method for the collection of various types of data through analysis of such a sample. On the basis of the data obtained by the method of the present invention for obtaining data, a doctor diagnoses urothelial cancer or squamous cancer.

The method of the present invention for obtaining data is not particularly limited, but can include the step of detecting ubiquilin 2 in the sample with a reagent for detecting ubiquilin 2 (hereinafter referred to as "detecting step"). The detecting step can be executed by detection of ubiquilin 2 in a biological sample at a protein level or at a genetic level. An explanation thereof has already been given. Further, as to the reagent for detecting ubiquilin 2 in the detecting step, the foregoing explanation of the "detection reagent" can be cited.

2. Treatment of Urothelial Cancer and Squamous Cancer with Ubiquilin 2

The inventors of the present invention confirmed in vitro (in vitro experiments) that as shown in Examples 2 and 3 below, suppression of ubiquilin 2 expression in urothelial cancer (i) can induce apoptosis in urothelial cancer and (ii) can enhance the sensitivity of urothelial cancer to an anticancer drug.

For this reason, a substance capable of suppressing ubiquilin 2 expression can serve as an anticancer drug for urothelial cancer and squamous cancer or as a substance for enhancing the sensitivity of cancer cells to an anticancer drug. Therefore, the present invention can also provide a method for screening an anticancer substance for urothelial cancer and squamous cancer (hereinafter referred to as "screening method of the present invention"). It should be noted that the term "anticancer substance" means a substance (anticancer drug additive) for enhancing the sensitivity of cancer cells to an anticancer drug, as well as an anticancer drug.

It should be noted here that the screening method of the present invention includes: comparing a level of ubiquilin 2 expression in urothelial cancer cells or squamous cancer cells brought into contact with a test article and a level of ubiquilin 2 expression in urothelial cancer cells or squamous cancer cells not brought into contact with a test article; and selecting a test article having an effect of reducing a level of ubiquilin 2 expression.

A method for the measurement of a level of ubiquilin 2 expression can be carried out with reference to the method for the detection of ubiquilin 2 in section [1. Detection of Urothelial Cancer and Squamous Cancer with Ubiquilin 2] above. For example, as for a sample containing urothelial cancer cells or squamous cancer cells brought into contact with a test article and a sample containing urothelial cancer cells or squamous cancer cells not brought into contact with a test article, the level of ubiquilin 2 expression in each of the samples can be measured by carrying out ELISA and/or flow cytometry with a ubiquilin 2 specific antibody.

Then, if the comparison between the levels of ubiquilin 2 expression in the respective samples shows that the level of ubiquilin 2 expression in the former sample is lower than that in the latter, it can be judged that the test article used then is highly likely to be an anticancer substance.

It should be noted that as for conditions for contact with urothelial cancer cells or squamous cancer cells, it is only necessary to consider and adopt optimum conditions for the types and states of test article and urothelial cancer cells or squamous cancer cells.

An example of a substance capable of inhibiting ubiquilin 2 expression is, but is not particularly limited to, the ubiquilin 2 gene or the siRNA of a partial polynucleotide thereof. The siRNA (short interference RNA, small interfering RNA) is not particularly limited in its base sequence provided it can suppress the expression of the target gene on the basis of the principle of RNAi.

The term "siRNA" as used herein is meant to encompass stRNA (small temporal RNA) and shRNA (short hairpin RNA). Further, the base sequence of siRNA is designed by a publicly-known method on the basis of base sequence information of the gene whose expression needs to be suppressed. At present, software for use in the design of siRNA is commercially available, and from the efficiency standpoint, it is preferable that the siRNA be designed using the software. Examples of the commercially-available software include siDirect (trademark) from RNAi, Inc. (http://www.rnai.co.jp/), etc.

The siRNA thus designed can be synthesized by a publicly-known automated nucleotide synthesizer. At present, the whole process from design to synthesis of siRNA can be entrusted to a company. Examples of entrustees include Ambion, Inc., Invitrogen Corporation, QIAGEN, Dharmacon, Inc., etc. In the Examples described below, experiments were conducted using the siRNA of SEQ ID NO. 4 as ubiquilin 2 siRNA. It is apparent to a person skilled in the art that siRNA for use in the present invention is not limited to the siRNA of SEQ ID NO. 4 provided it functions as ubiquilin 2 siRNA.

The present invention provides a substance that inhibits ubiquilin 2 expression (hereinafter referred to as "ubiquilin 2 inhibitor") found by the screening method of the present invention and an anticancer drug for urothelial cancer and squamous cancer (hereinafter referred to as "anticancer drug of the present invention) that contains ubiquilin 2 siRNA.

The anticancer drug of the present invention needs only be the ubiquilin 2 inhibitor or one that contains at least ubiquilin 2 siRNA, but may be combined with a desired pharmaceutically-acceptable carrier to form a composition. Examples of the carrier include sterilized water, saline, a buffering agent, vegetable oil, an emulsifier, a suspension, salt, a stabilizer, a preservative, a surfactant, a sustained-release drug, other proteins (such as BSA), transfection reagents (including lipofection reagents, liposomes, etc.), etc. Further usable examples of the carrier include glucose, lactose, gum arabic, gelatin, mannitol, starch paste, magnesium trisilicate, talc, corn starch, ceratin, colloid silica, potato starch, urea, hyaluronic acid, extracellular matrix substances such as collagen, polylactic acid, a calcium phosphate carrier, etc.

Further, in a case where the anticancer drug of the present invention contains siRNA, it may additionally contain a publicly-known reagent that is used in the introduction of siRNA into cells, such as Lipofectamine 2000 (Invitrogen Corporation) or RNAiFect (trademark) Transfection Reagent (QIAGEN). This is because such reagents as these improve the efficiency of the introduction of siRNA into cells and improve the stability of siRNA.

The formulation of the anticancer drug of the present invention is not limited, and may for example be a solution (injection), a microcapsule, a tablet, etc. The administration of the anticancer drug of the present invention may be either systemic or local, but local administration is preferred in a case where systemic administration entails a side effect or decreases effectiveness.

Conditions for the administration of the anticancer drug of the present invention for clinical applications can be determined as appropriate using conventional model animal systems or the like. That is, conditions under which appropriate prophylactic and therapeutic effects are obtained can be determined by considering conditions for administration such as dosage, intervals of administration, and routes of administration.

Further, administration to a patient can be, but is not limited to, surgical, transdermal, intranasal, transbronchial, intramuscular, interperitoneal, intravenous, intraarticular, subcutaneous, spinally intracavitary, intracerebroventricular, or oral, depending on the nature of various types of cell, disease, etc. Administration is either systemic or local, but local administration to the involved area is preferred in a case where systemic administration entails a problematic side effect. A person skilled in the art can appropriately select dosage and a way of administration, although dosages and ways of administration may vary depending on the tissue transitivity of an effective ingredient of the present medicine, the therapeutic goal, the weight, age, symptom, etc. of the patient.

Individuals to be treated are in principle humans, but may alternatively be pet animals (pets). Examples of pet animals include non-human mammals such as mice, rats, rabbits, cats, dogs, monkeys, horses, sheep, and cows and other vertebrate animals.

Further, the present invention also provides an anticancer drug additive (hereinafter referred to as "additive of the present invention"), used in combination with an anticancer drug for urothelial cancer and squamous cancer, for enhancing the sensitivity of cancer cells to the anticancer drug. The additive of the present invention may contain the ubiquilin 2 inhibitor found by the screening method or ubiquilin 2 siRNA. The additive of the present invention may be added to a conventionally publicly-known anticancer drug to be formulated, or may be formulated alone to be used in combination with a conventionally publicly-known anticancer drug.

An example of an anticancer drug for urothelial cancer is, but is not particularly limited to, gemcitabine (Eli Lilly 86 Co.). Further, an example of an anticancer drug for squamous cancer is cisplatin (Yakult Honsha Co., Ltd.).

Further, an endoplasmic reticulum stress agent, such as thapsigargin, which was used in Example 3 can also be used as an anticancer drug (References: *Jikken Igaku* [Experimental Medicine], March 2009 Issue, Vol. 27, No. 4, "Protein Homeostasis wo Kaimei suru-Shôhôtai Sutoresu to Shikkan" [Elucidating Protein Homeostasis-Endoplasmic Reticulum Stress and Disease]; and *Cancer Frontier* 2008 Vol. 10 3. Shôhôtai Sutoresu to Gan Chiryô [3. Endoplasmic Reticulum Stress and Cancer Treatment] (Saito, S. and Tomita, A.)).

3. Example Applications of the Present Invention

Further, the ubiquilin 2 specific antibody can be used to localize diseased tissue of urothelial cancer or squamous cancer in a living organism. Moreover, this technique can be applied to give correct treatment to an affected area where diseased tissue of urothelial cancer or squamous cancer is localized, and to thereby achieve efficient treatment. For example, while there have been cases of conventional tumor excision where complete resection of a tumor whose extent is not definite requires a comparatively large area including the area with suspected tumor, the ubiquilin 2 specific antibody can be used to definitely identify the extent of resection, thereby allowing efficient resection of the target tumor only.

An example of a method for labeling diseased tissue with ubiquilin 2 is a publicly-known fluorescent antibody technique. The fluorescent antibody technique may be either a technique for labeling cancer tissue by fluorescently labeling a ubiquilin 2 specific antibody and binding it to diseased tissue (direct fluorescent antibody technique) or a technique for labeling cancer tissue by binding an unlabeled ubiquilin 2 specific antibody to diseased tissue and then binding a labeled secondary antibody (anti-immunoglobulin antibody) to the diseased tissue (indirect fluorescent antibody technique).

It should be noted that the present invention can be expressed as follows:

In order to attain the foregoing object, a kit according to the present invention for detecting urothelial cancer and squamous cancer contains a reagent for detecting ubiquilin 2 in a sample.

Further, in the kit, the reagent may contain a ubiquilin 2 specific antibody.

Further, in the kit, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the kit, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the kit, the urothelial cancer may be one or more members selected from among renal pelvis cancer, ureteral cancer, and bladder cancer, and the squamous cancer may be one or more members selected from among cervical cancer and esophageal cancer.

Meanwhile, in order to attain the foregoing object, a device according to the present invention for automated diagnosis of urothelial cancer and squamous cancer include a ubiquilin 2 detection section for detecting ubiquilin 2 in a sample.

Further, in the device, the ubiquilin 2 detection section may be capable of detecting coloring, luminescence, or fluorescence from a sample treated with a reagent for detecting ubiquilin 2.

Further, in the device, the reagent may contain a ubiquilin 2 specific antibody.

Further, in the device, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the device, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the device, the sample may be a sample obtained from a living organism.

Further, in the device, the urothelial cancer may be one or more members selected from among renal pelvis cancer, ureteral cancer, and bladder cancer, and the squamous cancer may be one or more members selected from among cervical cancer and esophageal cancer.

Meanwhile, a method for obtaining data for diagnosis of urothelial cancer and squamous cancer includes detecting ubiquilin 2 in a sample obtained from a living organism.

The method may further include detecting ubiquilin 2 in the sample with a reagent for detecting ubiquilin 2.

Further, in the method, the reagent may contain a ubiquilin 2 specific antibody.

Further, in the method, the ubiquilin 2 specific antibody may be an antibody that is induced with a polypeptide of (1) or (2) and that binds specifically to the polypeptide: (1) a polypeptide consisting of the amino acid sequence of SEQ ID NO. 1; and (2) a partial polypeptide of the polypeptide (1).

Further, in the method, the reagent may contain a polynucleotide that hybridizes under stringent conditions with a polynucleotide of any of (3) to (5): (3) a polynucleotide consisting of the base sequence of SEQ ID NO. 2; (4) an antisense strand of the polynucleotide consisting of the base sequence of SEQ ID NO. 2; and (5) a polynucleotide consisting of a partial base sequence of the polynucleotide (3) or (4).

Further, in the method, the sample may be urine.

Further, in the method, the urothelial cancer may be one or more members selected from among renal pelvis cancer, ureteral cancer, and bladder cancer, and the squamous cancer may be one or more members selected from among cervical cancer and esophageal cancer.

Meanwhile, a method according to the present invention for screening an anticancer substance for urothelial cancer and squamous cancer includes: comparing a level of ubiquilin 2 expression in urothelial cancer cells or squamous cancer cells brought into contact with a test article and a level of ubiquilin 2 expression in urothelial cancer cells or squamous cancer cells not brought into contact with a test article; and selecting a test article having an effect of reducing a level of ubiquilin 2 expression.

Meanwhile, an anticancer drug according to the present invention for urothelial cancer and squamous cancer contains a substance that inhibits ubiquilin 2 expression.

Further, in the anticancer drug, the substance may be a ubiquilin 2 gene or siRNA of a partial polynucleotide thereof.

Meanwhile, an anticancer drug additive according to the present invention is an anticancer drug additive, used in combination with an anticancer drug for urothelial cancer and squamous cancer, for enhancing the sensitivity of cancer cells to the anticancer drug, the anticancer drug additive containing a substance that inhibits ubiquilin 2 expression.

Further, in the anticancer drug additive, the substance may be a ubiquilin 2 gene or siRNA of a partial polynucleotide thereof.

In the following, embodiments of the present invention are described in more detail by way of Examples. Of course, the present invention should not be limited to the Examples below, and it is needless to say that details can come in various aspects.

EXAMPLES

[Example 1] Immunohistological Staining and Immunocytological Staining with Use of a Ubiquilin 2 Specific Antibody (1) Experimental Methodology
<Construction of a Ubiquilin 2 Specific Antibody>
The ubiquilin 1 specific antibody, the ubiquilin 2 specific antibody, and the ubiquilin 2 specific antibody used were those purchased from Santa Cruz, Inc. Each of the antibodies was 500-fold diluted for use in experiment.
<Immunohistological Staining>
A patient specimen (i.e. a surgically-resected tissue sample) was formalin-fixed, and was then embedded in paraffin. A section was prepared, deparaffinized, rehydrated, and brought into reaction with a primary antibody (ubiquilin 2 specific antibody) (4° C., 18 hours). Then, after a peroxidase-labeled secondary antibody (Nichirei Corporation) was applied and an enzyme-specific substrate was added, the specimen wan stained with a coloring reagent.
<Immunocytological Staining: Method that Involves the Use of Urine Specimens>
Stained samples were prepared with urine specimens collected from patients (preparation of liquefied cytological specimens). Each urine specimen was fixed with 95% (v/v) alcohol (at a room temperature for 30 minutes), further brought into reaction with 0.5% hydrogen peroxide addition methanol and animal serum, and brought into reaction with a primary antibody (ubiquilin 2 specific antibody (for 30 minutes at room temperature). After that, the specimen was brought into reaction with a biotinated secondary antibody and peroxidase-labeled streptavidin and stained with a coloring reagent.

Each specimen in which twenty or more positive cells had been detected was found positive.
<Papanicolaou Staining>
A urine specimen was smeared on a glass slide and fixed with 95% (v/v) ethanol. The specimen was subjected to nuclear staining (staining with hematoxylin) and cytoplasmic staining (staining with an OG100 stain solution and an EA100 stain solution) and sealed in with a glass cover. On the basis of observation and structural atypia of the nucleus and cytoplasm, cancer cells were distinguished from non-tumor cells.

(2) Results
FIG. 1 shows results of immunohistological staining with a ubiquilin 2 specific antibody. (a) and (b) of FIG. 1 show results obtained from normal urothelia. (c) and (d) of FIG. 1 show results of obtained from non-invasive urothelial cancer (low malignant). (e) and (f) of FIG. 1 show results obtained from invasive urothelial cancer (highly malignant).

Brown-stained portions of FIG. 1 indicate sites of ubiquilin 2 expression. Whereas no staining was observed in normal urothelia ((a) and (b) of FIG. 1), brown staining was observed in urothelial cancer ((e) and (f) of FIG. 1). Further, brown staining was observed in low-malignant non-invasive urothelial cancer ((c) and (d) of FIG. 1), as well as in highly-malignant invasive urothelial cancer ((e) and (f) of FIG. 1). This showed that ubiquilin 2 was expressed specifically in urothelial cancer, and it was therefore confirmed that urothelial cancer can be detected by the ubiquilin 2 specific antibody.

Figure 2:
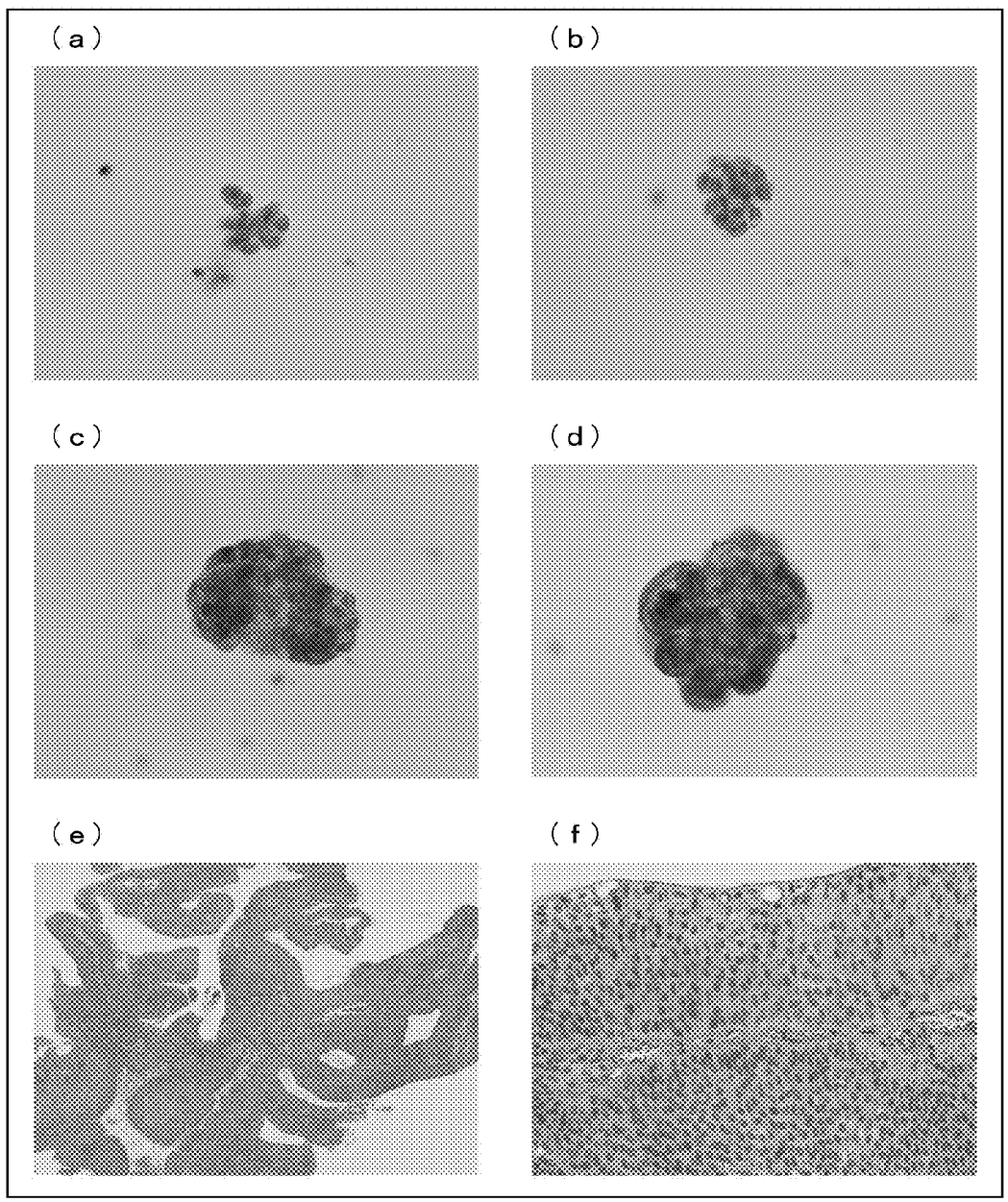
FIG. 2 is a set of photographs (a) to (f) showing results of various types of staining of a urine specimen and diseased tissue that were obtained from a patient diagnosed as urothelial cancer by histopathological diagnosis, the photographs (a) and (b) showing results of Papanicolaou staining of urinary exfoliated cells, the photographs (c) and (d) showing results of immunocytological staining of urinary exfoliated cells with a ubiquilin 2 specific antibody, the photographs (e) and (f) showing results of HE staining of diseased tissue obtained from the patient.

FIG. 2 shows results of various types of staining of a urine specimen and diseased tissue that were obtained from a patient diagnosed as urothelial cancer by histopathological diagnosis. (a) and (b) of FIG. 2 show results of Papanicolaou staining of urinary exfoliated cells. (c) and (d) of FIG. 2 show results of immunocytological staining of urinary exfoliated cells with a ubiquilin 2 specific antibody. (e) and (f) of FIG. 2 show results of HE staining of diseased tissue obtained from the patient.

Atypical cells were observed in usual urine cytodiagnosis, but could not go so far as to be diagnosed as cancer ((a) and (b) of FIG. 2). Meanwhile, urinary exfoliated cells from the same patient were stained brown as a result of staining with a ubiquilin 2 specific antibody ((c) and (d) of FIG. 2). The patient was diagnosed as non-invasive urothelial cancer (low malignant) as a result of histopathological diagnosis ((e) and (f) of FIG. 2).

Figure 3:
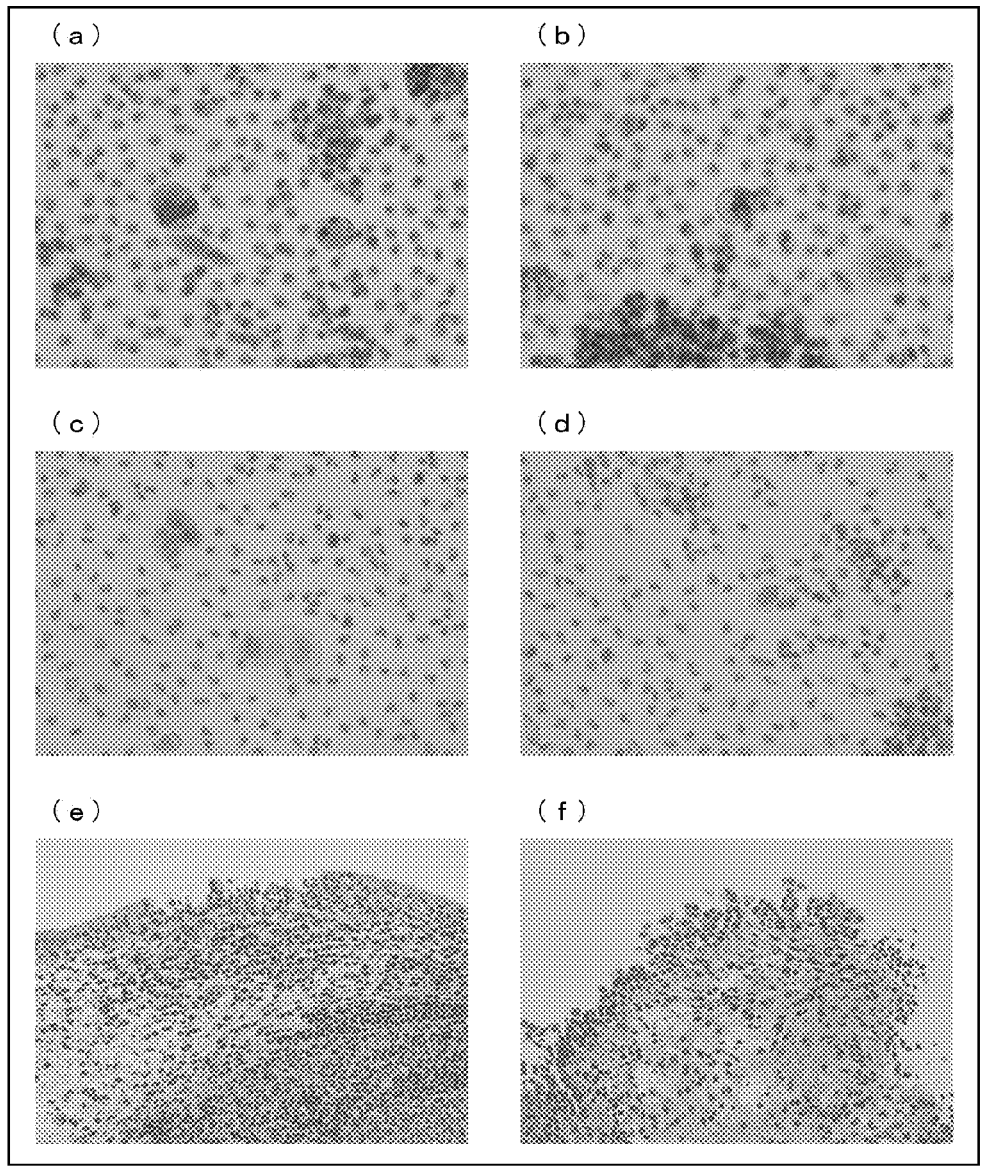
FIG. 3 is a set of photographs (a) to (f) showing results of various types of staining of a urine specimen and diseased tissue that were obtained from a patient diagnosed as non-neoplastic by histopathological diagnosis, the photographs (a) and (b) showing results of Papanicolaou staining of urinary exfoliated cells, the photographs (c) and (d) showing results of immunocytological staining of urinary exfoliated cells with a ubiquilin 2 specific antibody, the photographs (e) and (f) showing results of HE staining of urothelia obtained from the patient.

FIG. 3 shows results of various types of staining of a urine specimen and diseased tissue that were obtained from a patient diagnosed as non-neoplastic by histopathological diagnosis. (a) and (b) of FIG. 3 show results of Papanicolaou staining of urinary exfoliated cells. (c) and (d) of FIG. 3 show results of immunocytological staining of urinary exfoliated cells with a ubiquilin 2 specific antibody. (e) and (f) of FIG. 3 show results of HE staining of urothelia obtained from the patient.

Atypical cells were observed in usual urine cytodiagnosis, but could not go so far as to be diagnosed as cancer ((a) and (b) of FIG. 3). Meanwhile, urinary exfoliated cells from the same patient were not stained brown as a result of staining with a ubiquilin 2 specific antibody ((c) and (d) of FIG. 3). The patient was diagnosed as non-neoplastic as a result of histopathological diagnosis ((e) and (f) of FIG. 3).

It was confirmed from the results shown in FIGS. 2 and 3 that even in a case where a diagnosis of cancer cannot be made with usual urine cytodiagnosis, there is a possibility that a diagnosis of cancer may be made by immunostaining with a ubiquilin 2 specific antibody.

FIG. 4 shows results of comparison between (i) results of the diagnosis of urothelial cancer on the basis of results of Papanicolaou staining of urinary exfoliated cells (i.e. results of the conventional urine cytodiagnosis) and (ii) results of the diagnosis of urothelial cancer on the basis of results of immunocytological staining of urinary exfoliated cells with a ubiquilin 2 specific antibody (i.e. results of the urine cytodiagnosis according to the present invention).

(a) of FIG. 4 shows a breakdown of the subjects. "NEGATIVE (NORMAL)" shows the number of urine specimens (100 specimens) obtained from patients diagnosed as non-neoplastic by histopathological diagnosis. "POSITIVE (CANCER)" shows the number of urine specimens (49 specimens) obtained from patients diagnosed as urothelial cancer by histopathological diagnosis. That is, (a) of FIG. 4 shows that the conventional urine cytodiagnosis and the urine cytodiagnosis according to the present invention were performed on a total of 149 specimens. In (a) of FIG. 4, "HIGHLY MALIGNANT" shows the number of urine specimens (27 specimens) obtained from patients judged as highly malignant by histopathological diagnosis, and "LOW MALIGNANT" shows the number of urine specimens (22 specimens) obtained from patients judged as low malignant by histopathological diagnosis.

(b) of FIG. 4 shows results of the conventional urine cytodiagnosis of positive (cancer) urine specimens. As a result of the conventional urine cytodiagnosis, 20 out of the 27 highly-malignant cancer specimens were correctly found positive (sensitivity 74.1%). Meanwhile, only 5 out of the 22 low-malignant cancer specimens were correctly found positive (sensitivity 22.7%).

(c) of FIG. 4 shows results of the urine cytodiagnosis according to the present invention of positive (cancer) urine specimens. As a result of the urine cytodiagnosis according to the present invention, 27 out of the 27 highly-malignant cancer specimens were correctly found positive (sensitivity 100%). Meanwhile, 19 out of the 22 low-malignant cancer specimens were correctly found positive (sensitivity 86.4%).

(d) of FIG. 4 shows results of the conventional urine cytodiagnosis of negative (normal) urine specimens. As a result of the conventional urine cytodiagnosis, 0% of the non-neoplastic patients were found positive. Further, 13 specimens were found difficult to determine.

(e) of FIG. 4 shows results of the urine cytodiagnosis according to the present invention of negative (normal) urine specimens. As a result of the urine cytodiagnosis according to the present invention, 4% of the specimens were found difficult to determine because the number of urinary exfoliated cells was small, but 96% of the specimens were correctly found negative. Therefore, the specificity of the urine cytodiagnosis according to the present invention was 96%.

It was therefore confirmed from the results shown in FIG. 4 that the conventional urine cytodiagnosis allows diagnosis of highly-malignant specimens with a comparatively high sensitivity but exhibits a markedly lower sensitivity for low-malignant specimens, and that the conventional urine cytodiagnosis has a comparatively high specificity. On the other hand, it was confirmed that the urine cytodiagnosis according to the present invention allows diagnosis of urothelial cancer with high sensitivity and high specificity. Furthermore, the urine cytodiagnosis according to the present invention exhibited an advantage of allowing diagnosis of even low-malignant specimens with high sensitivity.

Figure 5:
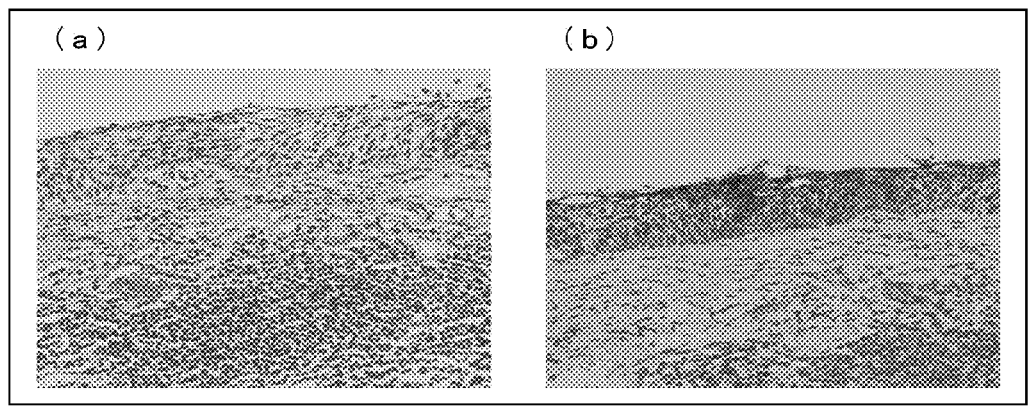
FIG. 5 is a set of photographs (a) and (b) showing a result of HE staining of diseased tissue collected from an esophageal squamous cancer patient and a result of immunostaining of the diseased tissue with a ubiquilin 2 specific antibody, respectively, the photograph (a) showing a result of HE staining of diseased tissue, the photograph (b) showing a result of immunostaining of the diseased tissue with a ubiquilin 2 specific antibody.

FIG. 5 shows a result of HE staining of diseased tissue collected from an esophageal squamous cancer patient and a result of immunostaining of the diseased tissue with a ubiquilin 2 specific antibody. (a) of FIG. 5 shows a result of HE staining of diseased tissue, and (b) of FIG. 5 shows a result of immunostaining of the diseased tissue with a ubiquilin 2 specific antibody.

It was confirmed from FIG. 5 that the ubiquilin 2 specific antibody allows detection of esophageal squamous cancer as well as urothelial cancer.

Figure 6:
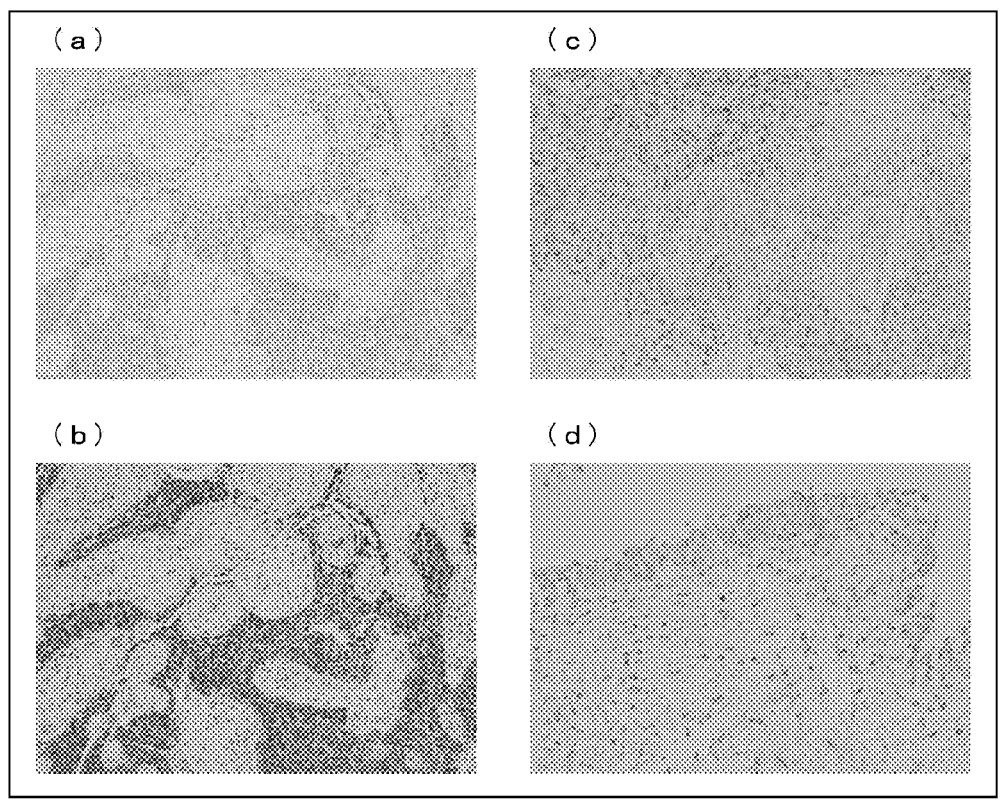
FIG. 6 is a set of photographs (a) to (d) showing results of immunostaining of diseased tissue of bladder cancer (urothelial cancer) with a ubiquilin 1, 2, or 4 specific antibody, the photograph (a) showing a result of immunostaining of diseased tissue with a ubiquilin 1 specific antibody, the photograph (b) showing a result of immunostaining of diseased tissue with a ubiquilin 2 specific antibody, the photograph (c) showing a result of immunostaining of diseased tissue with a ubiquilin 4 specific antibody, the photograph (d) showing a result of immunostaining of normal urothelial tissue with a ubiquilin 2 specific antibody.

Next, ubiquilin 2 was compared with other members of the ubiquilin family (ubiquilin 1 and ubiquilin 4). FIG. 6 shows results of immunostaining of diseased tissue of bladder cancer (urothelial cancer) with a ubiquilin 1, 2, or 4 specific antibody. (a) of FIG. 6 shows a result of immunostaining of diseased tissue with a ubiquilin 1 specific antibody. (b) of FIG. 6 shows a result of immunostaining of diseased tissue with a ubiquilin 2 specific antibody. (c) of FIG. 6 shows a result of immunostaining of diseased tissue with a ubiquilin 4 specific antibody. (d) of FIG. 6 shows a result of immunostaining of normal urothelial tissue with a ubiquilin 2 specific antibody. It was confirmed from FIG. 6 that the diseased tissue of bladder cancer was stained brown only in the case where the ubiquilin 2 specific antibody was used (see (b) of FIG. 6). It was therefore confirmed that whereas neither ubiquilin 1 nor 4 allows detection of bladder cancer, ubiquilin 2 allows clear detection of bladder cancer.

Figure 7:
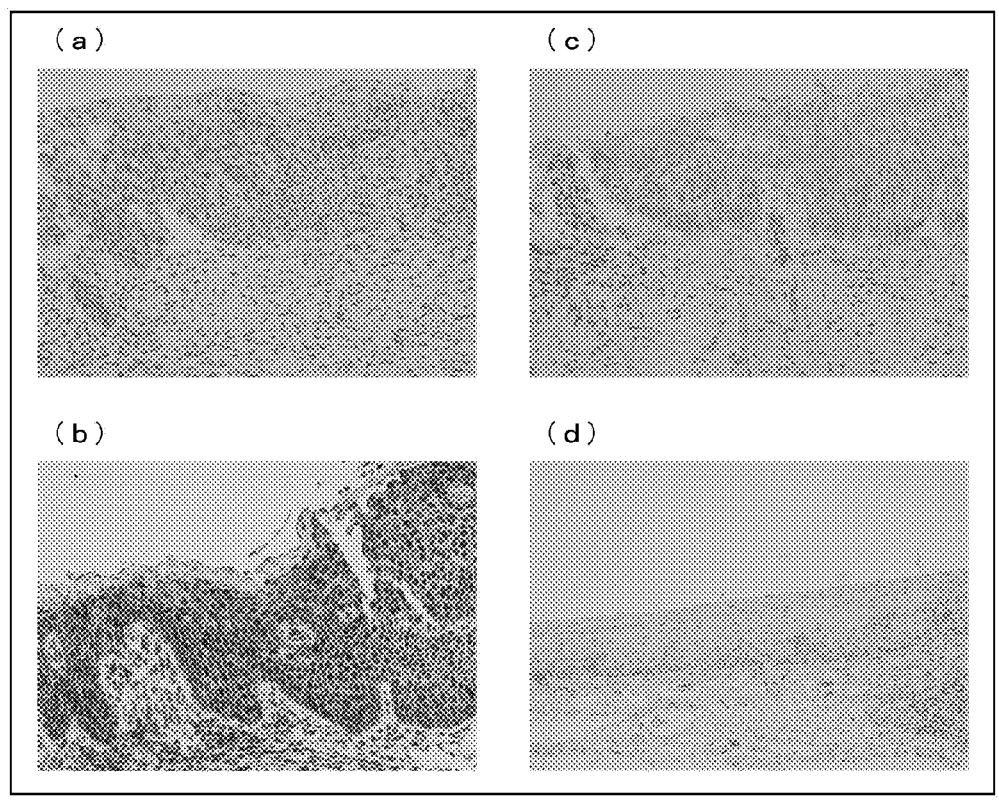
FIG. 7 is a set of photographs (a) to (d) showing results of immunostaining of diseased tissue of cervical cancer (squamous cancer) with a ubiquilin 1, 2, or 4 specific antibody, the photograph (a) showing a result of immunostaining of diseased tissue with a ubiquilin 1 specific antibody, the photograph (b) showing a result of immunostaining of diseased tissue with a ubiquilin 2 specific antibody, the photograph (c) showing a result of immunostaining of diseased tissue with a ubiquilin 4 specific antibody, the photograph (d) showing a result of immunostaining of normal cervical squamous tissue with a ubiquilin 2 specific antibody.

FIG. 7 shows results of immunostaining of diseased tissue of cervical cancer (squamous cancer) with a ubiquilin 1, 2, or 4 specific antibody. (a) of FIG. 7 shows a result of immunostaining of diseased tissue with a ubiquilin 1 specific antibody. (b) of FIG. 7 shows a result of immunostaining of diseased tissue with a ubiquilin 2 specific antibody. (c) of FIG. 7 shows a result of immunostaining of diseased tissue with a ubiquilin 4 specific antibody. (d) of FIG. 7 shows a result of immunostaining of normal cervical squamous tissue with a ubiquilin 2 specific antibody. It was confirmed from FIG. 7 that the diseased tissue of cervical cancer was stained brown only in the case where the ubiquilin 2 specific antibody was used (see (b) of FIG. 7). It was therefore confirmed that whereas neither ubiquilin 1 nor 4 allows detection of cervical cancer, ubiquilin 2 allows clear detection of cervical cancer.

Figure 8:
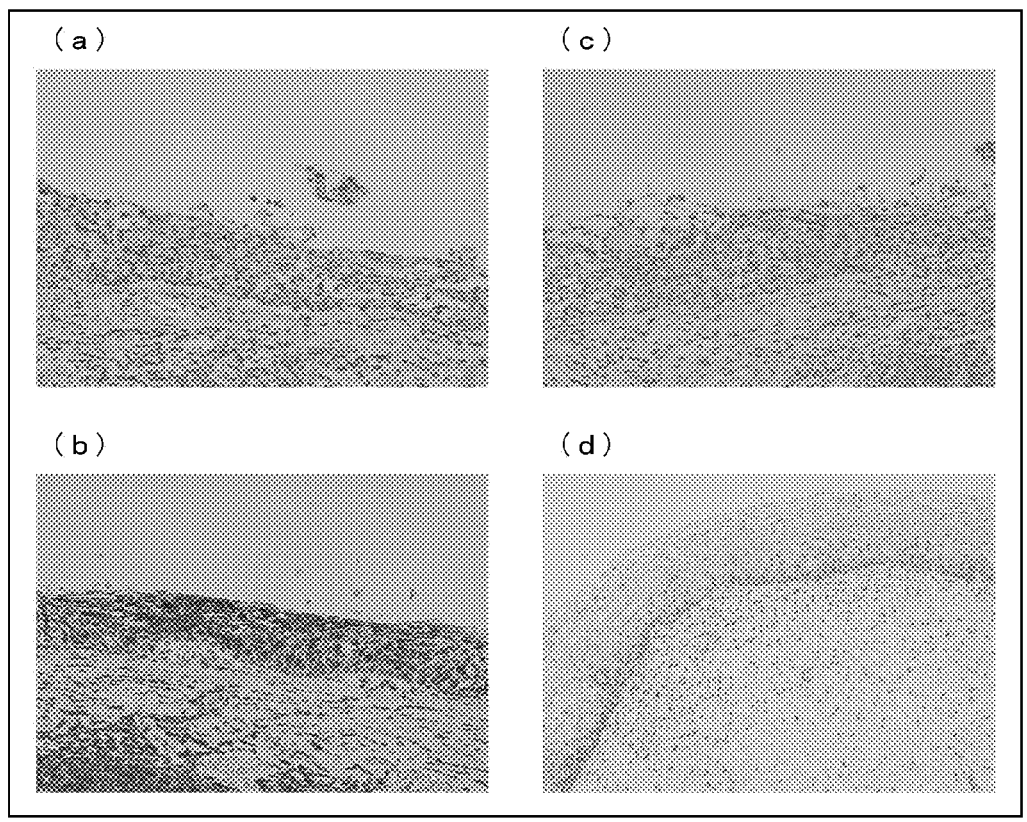
FIG. 8 is a set of photographs (a) to (d) showing results of immunostaining of diseased tissue of esophageal cancer (squamous cancer) with a ubiquilin 1, 2, or 4 specific antibody, the photograph (a) showing a result of immunostaining of diseased tissue with a ubiquilin 1 specific antibody, the photograph (b) showing a result of immunostaining of diseased tissue with a ubiquilin 2 specific antibody, the photograph (c) showing a result of immunostaining of diseased tissue with a ubiquilin 4 specific antibody, the photograph (d) showing a result of immunostaining of normal esophageal tissue with a ubiquilin 2 specific antibody.

FIG. 8 shows results of immunostaining of diseased tissue of esophageal cancer (squamous cancer) with a ubiquilin 1, 2, or 4 specific antibody. (a) of FIG. 8 shows a result of immunostaining of diseased tissue with a ubiquilin 1 specific antibody. (b) of FIG. 8 shows a result of immunostaining of diseased tissue with a ubiquilin 2 specific antibody. (c) of FIG. 8 shows a result of immunostaining of diseased tissue with a ubiquilin 4 specific antibody. (d) of FIG. 8 shows a result of immunostaining of normal esophageal tissue with a ubiquilin 2 specific antibody. It was confirmed from FIG. 8 that the diseased tissue of esophageal cancer was stained brown only in the case where the ubiquilin 2 specific antibody was used (see (b) of FIG. 8). It was therefore confirmed that whereas neither ubiquilin 1 nor 4 allows detection of esophageal cancer, ubiquilin 2 allows clear detection of esophageal cancer.

FIG. 9 shows a result of HE staining of diseased tissue of renal cancer (see (a) of FIG. 9) and a result of immunostaining of diseased tissue of renal cancer with a ubiquilin 2 specific antibody (see (b) of FIG. 9).

Figure 10:
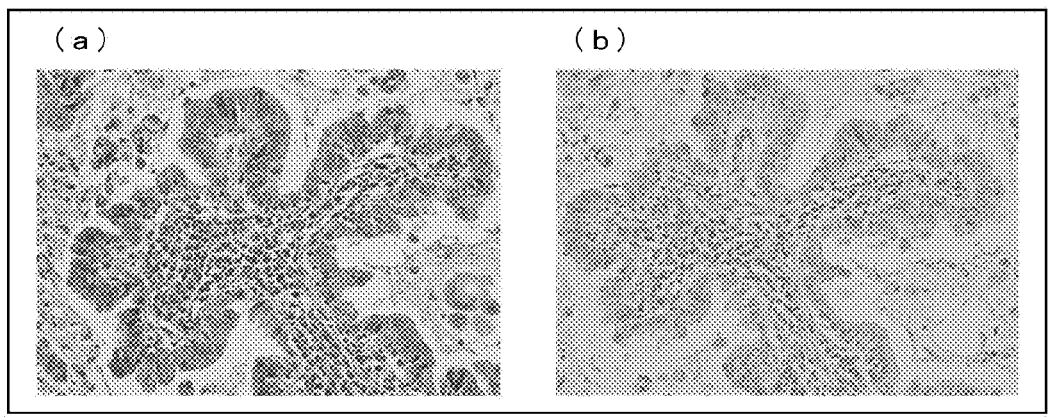
FIG. 10 is a set of photographs (a) and (b), the photograph (a) showing a result of HE staining of diseased tissue of pulmonary adenocarcinoma, the photograph (b) showing a result of immunostaining of diseased tissue of pulmonary adenocarcinoma with a ubiquilin 2 specific antibody.

FIG. 10 shows a result of HE staining of diseased tissue of pulmonary adenocarcinoma (see (a) of FIG. 10) and a result of immunostaining of diseased tissue of pulmonary adenocarcinoma with a ubiquilin 2 specific antibody (see (b) of FIG. 10).

According to the results shown in FIGS. 9 and 10, ubiquilin 2 was hardly expressed in renal cancer and pulmonary adenocarcinoma. It was therefore confirmed that renal cancer and pulmonary adenocarcinoma cannot be detected by detecting ubiquilin 2.

Figure 11:
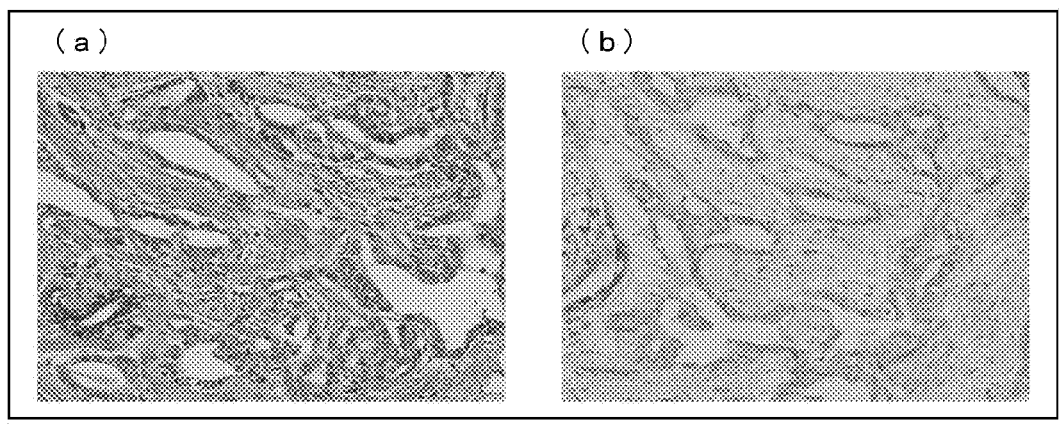
FIG. 11 is a set of photographs (a) and (b), the photograph (a) showing a result of HE staining of diseased tissue of large intestinal adenoma, the photograph (b) showing a result of immunostaining of diseased tissue of intestinal adenoma with a ubiquilin 2 specific antibody.

FIG. 11 shows a result of HE staining of diseased tissue of intestinal adenoma (see (a) of FIG. 11) and a result of immunostaining of diseased tissue of intestinal adenoma with a ubiquilin 2 specific antibody (see (b) of FIG. 11).

According to the results shown in FIG. 11, ubiquilin 2 expression was observed in intestinal adenoma, but the expression signal was very weak. Further, a higher level of ubiquilin 2 expression was observed in some of the diseased tissue of intestinal adenoma (data not shown), and the expression of ubiquilin 2 lacked stability. It was therefore confirmed that it is difficult to detect intestinal adenoma by detecting ubiquilin 2.

FIG. 12 shows a result of HE staining of diseased tissue of breast cancer and results of immunostaining of the diseased tissue with a ubiquilin 1, 2, or 4 specific antibody. (a) of FIG. 12 shows a result of HE staining. (b) of FIG. 12 shows a result of immunostaining of diseased tissue with a ubiquilin 2 specific antibody. (c) of FIG. 12 shows a result of immunostaining of diseased tissue with a ubiquilin 1 specific antibody. (d) of FIG. 12 shows a result of immunostaining of diseased tissue with a ubiquilin 4 specific antibody.

Figure 13:
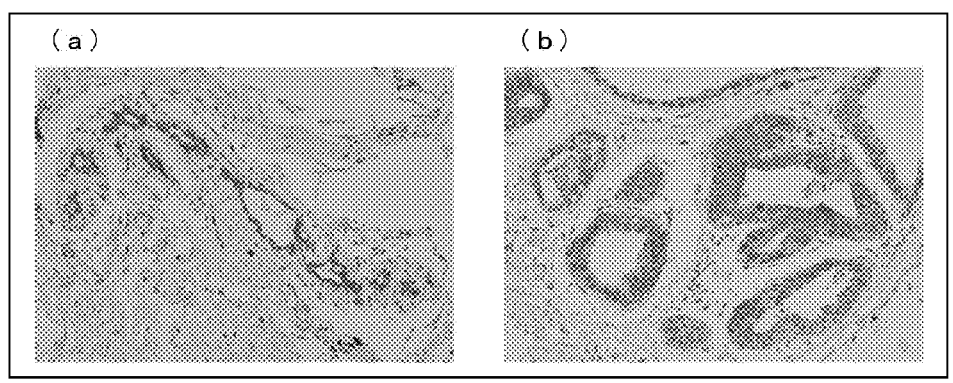
FIG. 13 is a set of photographs (a) and (b) showing results of immunostaining of normal mammary gland with a ubiquilin 2 specific antibody.

FIG. 13 shows results of immunostaining of normal mammary gland with a ubiquilin 2 specific antibody. Both (a) and (b) of FIG. 13 show results of immunostaining of normal mammary gland.

FIGS. 12 and 13 show that high levels of ubiquilin 2 expression were observed in both breast cancer and normal mammary gland (see (b) of FIG. 12 and FIG. 13). Further, as in the case of ubiquilin 2, high levels of ubiquilin 1 and 4 expression were confirmed in the diseased tissue of breast cancer (see (c) and (d) of FIG. 12). It was therefore confirmed that it is difficult to detect breast cancer by detecting ubiquilin 2.

Figure 14:
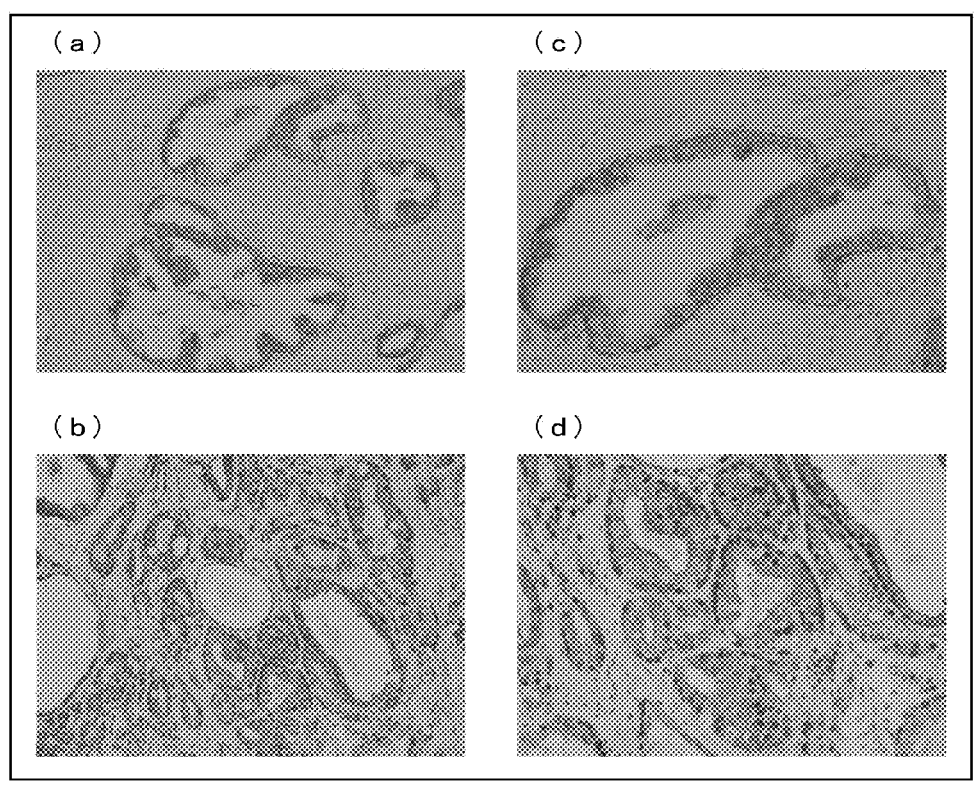
FIG. 14 is a set of photographs (a) to (d) showing results of immunostaining of diseased tissue of prostate cancer or normal prostate tissue with a ubiquilin 2 specific antibody, the photographs (a) and (c) showing results of immunostaining of diseased tissue of prostate cancer, the photographs (b) and (d) showing results of immunostaining of normal prostate tissue.

FIG. 14 shows results of immunostaining of diseased tissue of prostate cancer or normal prostate tissue with a ubiquilin 2 specific antibody. (a) and (c) of FIG. 14 show results of immunostaining of diseased tissue of prostate cancer, and (b) and (d) of FIG. 14 show results of immunostaining of normal prostate tissue.

FIG. 14 shows that high levels of ubiquilin 2 expression were observed in both the diseased tissue of prostate cancer and normal prostate tissue. It was therefore confirmed that it is difficult to detect prostate cancer by detecting ubiquilin 2.

[Example 2] Examination 1 of the Effects of Suppression of Ubiquilin 2 Gene Expression (1) Methodology Control RNA (QIAGEN) or ubiquilin 2 siRNA was introduced into human urothelial cancer cell strain KU7 (donated by the School of Urology at the Department of Medicine in Keio University). The ubiquilin 2 siRNA used was siRNA synthesized with 5'-TCCCATAAAGAGAC-CCTAATA-3' (SEQ ID NO. 3) of the ubiquilin 2 gene as a Target sequence. The introduction of each RNA was performed by a Lipofection technique with a Lipofectamine™ RNAimax (Life Technologies Japan Ltd.).

After 72 hours of culture of the cells transfected with the RNA, TUNEL positive cells (i.e. cells having undergone apoptosis) were detected under a fluorescence microscope by the TUNEL (Terminal deoxynucleotidyl transferase dUTP nick end labeling) technique, and the percentage of the TUNEL positive cells to the total number of cells was calculated.

Figure 15:
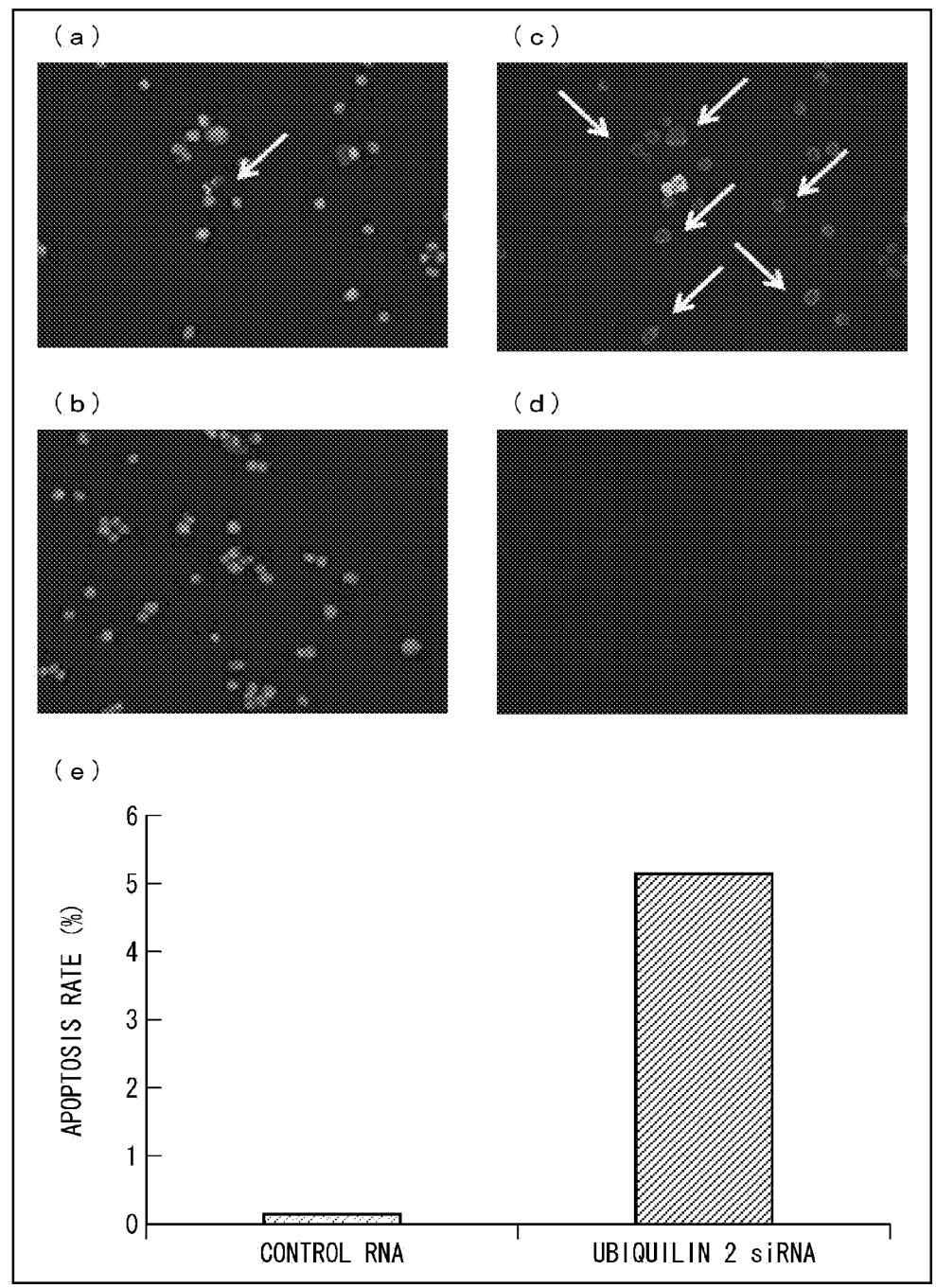
FIG. 15 is a set of photographs (a) to (d) and a histogram (e), the photograph (a) showing a result of DAPI staining of human urothelial cancer cell strain KU7 transfected with ubiquilin 2 siRNA and nuclear staining of the cells, the photograph (b) showing a result of DAPI staining of human urothelial cancer cell strain KU7 transfected with control RNA and nuclear staining of the cells, the photograph (c) showing a result of TUNEL staining of cells transfected with ubiquilin 2 siRNA and detection of TUNEL positive cells (cells having undergone apoptosis), the photograph (d) showing a result of TUNEL staining of cells transfected with control RNA and detection of TUNEL positive cells (cells having undergone apoptosis), the histogram (e) showing the calculated percentage of TUNEL positive cells (number of cells having undergone apoptosis) to DAPI positive cells (total number of cells).

(2) Results (a) of FIG. 15 shows a result of DAPI staining of cells transfected with ubiquilin 2 siRNA and nuclear staining of the cells. (b) of FIG. 15 shows a result of DAPI staining of cells transfected with control RNA and nuclear staining of the cells. Both (a) and (b) of FIG. 15 show that the nuclei of all of the cells were stained blue. The arrows in (a) of FIG. 15 indicate occurrences of DNA fragmentation.

(c) of FIG. 15 shows a result of TUNEL staining of cells transfected with ubiquilin 2 siRNA and detection of TUNEL positive cells (cells having undergone apoptosis). (d) of FIG. 15 shows a result of TUNEL staining of cells transfected with control RNA and detection of TUNEL positive cells (cells having undergone apoptosis). In (c) and (d) of FIG. 15, the cells colored green are TUNEL positive cells (cells having undergone apoptosis). The arrows in (c) of FIG. 15 indicate TUNEL positive cells.

(e) of FIG. 15 is a graph showing the calculated percentage (denoted as "APOPTOSIS RATE" in the drawing) of TUNEL positive cells (number of cells having undergone apoptosis) to DAPI positive cells (total number of cells).

It was confirmed from FIG. 15 that apoptosis (death of cells) was induced in the cancer cells by disrupting (knocking down) the ubiquilin 2 gene. This means that it was confirmed in vitro (in vitro experiment) that the disruption (knockdown) of in vitro experiment has a therapeutic effect on cancer.

[Example 3] Examination 2 of the Effects of Suppression of Ubiquilin 2 Gene Expression (1) Methodology To a culture solution prepared by culturing, for 24 hours, cells transfected with RNA in the same manner as in Example 2, thapsigargin (Sigma Corporation), which is an endoplasmic reticulum stress agent, was added so that predetermined concentrations (0.1 µM, 0.5 µM, 1 µM, and 2.5 µM) were achieved.

Seventy-two hours after the addition of thapsigargin, a cell survival assay (MTS assay: with use of a kit from Promega KK) was performed to obtain the number of cells that survived, and the ratio (cell survival rate) of the number of cells that survived in the presence of thapsigargin to the number of cells that survived in the absence of thapsigargin was calculated.

(2) Results

Figure 16:
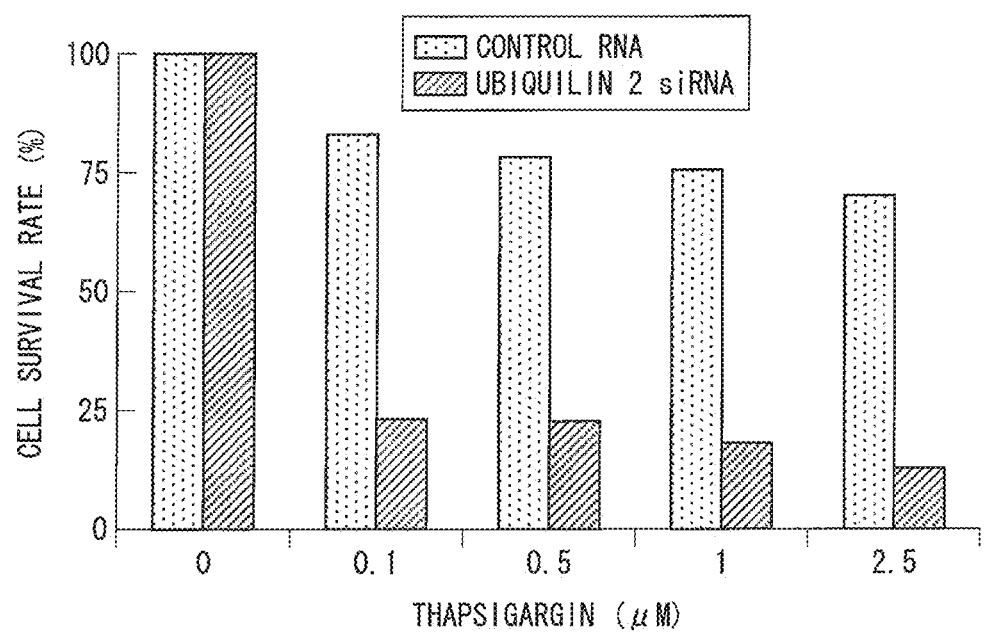
FIG. 16 is a histogram showing the respective cell survival rates of human urothelial cancer cell strain KU7 (donated by the School of Urology at the Department of Medicine in Keio University) transfected with ubiquilin 2 siRNA and human urothelial cancer cell strain KU7 transfected with control RNA, as observed 72 hours after the addition of thapsigargin (Wako Pure Chemical Industries, Ltd.), which is an endoplasmic reticulum stress agent, into the respective cell culture media.

FIG. 16 shows cell survival rates as observed 72 hours after the addition of thapsigargin. In a case where the ubiquilin 2 gene is not disrupted (knocked down), thapsigargin hardly exhibits cytotoxicity (see the results obtained from control RNA). On the other hand, thapsigargin exhibited markedly enhanced cytotoxicity in cells in which the ubiquilin 2 gene had been disrupted (knocked down).

An endoplasmic reticulum stress agent such as thapsigargin is a drug expected to be used as an anticancer drug for clinical applications (References: *Jikken Igaku* [Experimental Medicine], March 2009 Issue, Vol. 27, No. 4, "Protein Homeostasis wo Kaimei suru-Shôhôtai Sutoresu to Shikkan" [Elucidating Protein Homeostasis-Endoplasmic Reticulum Stress and Disease]; and *Cancer Frontier* 2008 Vol. 10 3. Shôhôtai Sutoresu to Gan Chiryô [3. Endoplasmic Reticulum Stress and Cancer Treatment] (Saito, S. and Tomita, A.)), and it was confirmed in vitro (in vitro experiment) that sensitivity to chemotherapy can be enhanced by disrupting (knocking down) the ubiquilin 2 gene and that there is a possibility of more effective treatment. It is expected that a novel treatment strategy will be formulated by disrupting (knocking down) the ubiquilin 2 gene.

INDUSTRIAL APPLICABILITY

As explicated above, the present invention allows easy detection or diagnosis of urothelial cancer (renal pelvis cancer, ureteral cancer, and bladder cancer) and squamous cancer (esophageal cancer, cervical cancer, etc.) by detecting ubiquilin 2. Further, the present invention allows the diagnosis of urothelial cancer and squamous cancer with high sensitivity (diagnostic accuracy) and high specificity.

Furthermore, disruption of ubiquilin 2 genes can induce apoptosis in cancer cells and enhance the sensitivity of cancer cells to an anticancer drug. For this reason, the present invention is highly expected to contribute to the treatment of urothelial cancer and squamous cancer.

Therefore, the present invention is industrially applicable, for example, in diagnostic and medical industries.

The invention claimed is:

1. A method for diagnosing urothelial cancer, the method comprising determining that a living organism has urothelial cancer by a method comprising:
   (i) obtaining a urine sample from a living organism, said urine sample comprising urinary exfoliated cells;
   (ii) detecting ubiquilin 2 in the urinary exfoliated cells in the urine sample with use of a ubiquilin 2 specific antibody and determining a protein concentration of the ubiquilin 2;
   (iii) comparing the protein concentration of the ubiquilin 2 in the urinary exfoliated cells in the urine sample to a protein concentration of ubiquilin 2 in urinary exfoliated cells in a urine sample obtained from a healthy subject; and
   (iv) diagnosing the living organism as having urothelial cancer in a case where the protein concentration of the ubiquilin 2 in the urinary exfoliated cells in the urine sample obtained from the living organism is significantly higher than the protein concentration of the ubiquilin 2 in the urinary exfoliated cells in the urine sample obtained from the healthy subject.

2. The method as set forth in claim 1, wherein the ubiquilin 2 specific antibody is an antibody that is induced with a polypeptide of (1) or (2) which serves as an antigen, and that binds specifically to the polypeptide:
- (1) a polypeptide consisting of the amino acid sequence of SEQ ID NO. 1; and
- (2) a partial polypeptide of the polypeptide (1).

3. The method as set forth in claim 1, wherein the urothelial cancer is one or more members selected from among renal pelvis cancer, ureteral cancer, and bladder cancer.

4. A method for diagnosing squamous cancer, the method comprising determining that a living organism has squamous cancer by a method comprising:
- (i) obtaining a sample from a living organism, said sample being phlegm or saliva each comprising squamous cells;
- (ii) detecting ubiquilin 2 in the squamous cells in the sample with use of a ubiquilin 2 specific antibody and determining a protein concentration of the ubiquilin 2;
- (iii) comparing the protein concentration of the ubiquilin 2 in the squamous cells in the sample to a protein concentration of ubiquilin 2 in squamous cells in a sample obtained from a healthy subject, the sample obtained from the healthy subject being phlegm or saliva; and
- (iv) diagnosing the living organism as having squamous cancer in a case where the protein concentration of the ubiquilin 2 in the squamous cells in the sample obtained from the living organism is significantly higher than the protein concentration of the ubiquilin 2 in the squamous cells in the sample obtained from the healthy subject.

5. The method as set forth in claim 4, wherein the squamous cancer is esophageal cancer.

* * * * *

SEQUENCE LISTING

<160> NUMBER OF SEQ ID NOS: 3

<210> SEQ ID NO 1
<211> LENGTH: 624
<212> TYPE: PRT
<213> ORGANISM: Homo sapiens

<400> SEQUENCE: 1

```
Met Ala Glu Asn Gly Glu Ser Ser Gly Pro Pro Arg Pro Ser Arg Gly
1               5                   10                  15

Pro Ala Ala Ala Gln Gly Ser Ala Ala Ala Pro Ala Glu Pro Lys Ile
            20                  25                  30

Ile Lys Val Thr Val Lys Thr Pro Lys Glu Lys Glu Glu Phe Ala Val
        35                  40                  45

Pro Glu Asn Ser Ser Val Gln Gln Phe Lys Glu Ala Ile Ser Lys Arg
    50                  55                  60

Phe Lys Ser Gln Thr Asp Gln Leu Val Leu Ile Phe Ala Gly Lys Ile
65                  70                  75                  80

Leu Lys Asp Gln Asp Thr Leu Ile Gln His Gly Ile His Asp Gly Leu
                85                  90                  95

Thr Val His Leu Val Ile Lys Ser Gln Asn Arg Pro Gln Gly Gln Ser
            100                 105                 110

Thr Gln Pro Ser Asn Ala Ala Gly Thr Asn Thr Thr Ser Ala Ser Thr
        115                 120                 125

Pro Arg Ser Asn Ser Thr Pro Ile Ser Thr Asn Ser Asn Pro Phe Gly
    130                 135                 140

Leu Gly Ser Leu Gly Gly Leu Ala Gly Leu Ser Ser Leu Gly Leu Ser
145                 150                 155                 160

Ser Thr Asn Phe Ser Glu Leu Gln Ser Gln Met Gln Gln Gln Leu Met
                165                 170                 175

Ala Ser Pro Glu Met Met Ile Gln Ile Met Glu Asn Pro Phe Val Gln
            180                 185                 190

Ser Met Leu Ser Asn Pro Asp Leu Met Arg Gln Leu Ile Met Ala Asn
        195                 200                 205

Pro Gln Met Gln Gln Leu Ile Gln Arg Asn Pro Glu Ile Ser His Leu
    210                 215                 220

Leu Asn Asn Pro Asp Ile Met Arg Gln Thr Leu Glu Ile Ala Arg Asn
225                 230                 235                 240

Pro Ala Met Met Gln Glu Met Met Arg Asn Gln Asp Leu Ala Leu Ser
                245                 250                 255

Asn Leu Glu Ser Ile Pro Gly Gly Tyr Asn Ala Leu Arg Arg Met Tyr
            260                 265                 270

Thr Asp Ile Gln Glu Pro Met Leu Asn Ala Ala Gln Glu Gln Phe Gly
        275                 280                 285

Gly Asn Pro Phe Ala Ser Val Gly Ser Ser Ser Ser Gly Glu Gly
    290                 295                 300
```

Thr Gln Pro Ser Arg Thr Glu Asn Arg Asp Pro Leu Pro Asn Pro Trp
305                 310                 315                 320

Ala Pro Pro Ala Thr Gln Ser Ser Ala Thr Thr Ser Thr Thr Thr Thr
            325                 330                 335

Ser Thr Gly Ser Gly Ser Gly Asn Ser Ser Asn Ala Thr Gly Asn
        340                 345                 350

Thr Val Ala Ala Ala Asn Tyr Val Ala Ser Ile Phe Ser Thr Pro Gly
            355                 360                 365

Met Gln Ser Leu Leu Gln Gln Ile Thr Glu Asn Pro Gln Leu Ile Gln
            370                 375                 380

Asn Met Leu Ser Ala Pro Tyr Met Arg Ser Met Met Gln Ser Leu Ser
385                 390                 395                 400

Gln Asn Pro Asp Leu Ala Ala Gln Met Met Leu Asn Ser Pro Leu Phe
            405                 410                 415

Thr Ala Asn Pro Gln Leu Gln Glu Gln Met Arg Pro Gln Leu Pro Ala
            420                 425                 430

Phe Leu Gln Gln Met Gln Asn Pro Asp Thr Leu Ser Ala Met Ser Asn
            435                 440                 445

Pro Arg Ala Met Gln Ala Leu Met Gln Ile Gln Gln Gly Leu Gln Thr
450                 455                 460

Leu Ala Thr Glu Ala Pro Gly Leu Ile Pro Ser Phe Thr Pro Gly Val
465                 470                 475                 480

Gly Val Gly Val Leu Gly Thr Ala Ile Gly Pro Val Gly Pro Val Thr
            485                 490                 495

Pro Ile Gly Pro Ile Gly Pro Ile Val Pro Phe Thr Pro Ile Gly Pro
            500                 505                 510

Ile Gly Pro Ile Gly Pro Thr Gly Pro Ala Ala Pro Pro Gly Ser Thr
            515                 520                 525

Gly Ser Gly Gly Pro Thr Gly Pro Thr Val Ser Ser Ala Ala Pro Ser
530                 535                 540

Glu Thr Thr Ser Pro Thr Ser Glu Ser Gly Pro Asn Gln Gln Phe Ile
545                 550                 555                 560

Gln Gln Met Val Gln Ala Leu Ala Gly Ala Asn Ala Pro Gln Leu Pro
            565                 570                 575

Asn Pro Glu Val Arg Phe Gln Gln Gln Leu Glu Gln Leu Asn Ala Met
            580                 585                 590

Gly Phe Leu Asn Arg Glu Ala Asn Leu Gln Ala Leu Ile Ala Thr Gly
            595                 600                 605

Gly Asp Ile Asn Ala Ala Ile Glu Arg Leu Leu Gly Ser Gln Pro Ser
            610                 615                 620

<210> SEQ ID NO 2
<211> LENGTH: 1875
<212> TYPE: DNA
<213> ORGANISM: Homo sapiens

<400> SEQUENCE: 2
atggctgaga atggcgagag cagcggcccc ccgcgcccct cccgcggccc tgctgcggcc      60
caaggctcgg ctgctgcccc ggctgagcct aaaatcatca agtcacggt gaagactccc      120 aaagagaaag aggagttcgc ggtgcccgag aacagctcgg ttcagcagtt taaggaagcg      180
atttcgaaac gcttcaaatc ccaaaccgat cagctagtgc tgattttttgc cggaaaaatc      240 ttaaaagatc aagataccctt gatccagcat ggcatccatg atgggctgac tgttcacctt      300

```
gtcatcaaaa gccagaaccg acctcagggc cagtccacgc agcctagcaa tgccgcggga    360
actaacacta cctcggcgtc gactcccagg agtaactcca cacctatttc cacaaatagc    420
aacccgtttg ggttggggag cctgggagga cttgcaggcc ttagcagcct gggcttgagc    480
tcgaccaact tctctgagct ccagagccag atgcagcagc agcttatggc cagccctgag    540
atgatgatcc aaataatgga aaatcccttt gttcagagca tgctttcgaa tcccgatctg    600
atgaggcagc tcattatggc taatccacag atgcagcaat tgattcagag aaacccagaa    660
atcagtcacc tgctcaacaa cccagacata atgaggcaga cactcgaaat tgccaggaat    720
ccagccatga tgcaagagat gatgagaaat caagacctgg ctcttagcaa tctagaaagc    780
atcccaggtg gctataatgc tttacggcgc atgtacactg acattcaaga gccgatgctg    840
aatgccgcac aagagcagtt tgggggtaat ccatttgcct ccgtggggag tagttcctcc    900
tctggggaag gtacgcagcc ttcccgcaca gaaaatcgcg atccactacc caatccatgg    960
gcaccaccgc cagctaccca gagttctgca actaccagca cgaccacaag cactggtagt   1020
gggtctggca atagttccag caatgctact gggaacaccg ttgctgccgc taattatgtc   1080
gccagcatct ttagtacccc aggcatgcag agcctgctgc aacagataac tgaaaacccc   1140
cagctgattc agaatatgct gtcggcgccc tacatgagaa gcatgatgca gtcgctgagc   1200
cagaatccag atttggctgc acagatgatg ctgaatagcc cgctgtttac tgcaaatcct   1260
cagctgcagg agcagatgcg gccacagctc ccagccttcc tgcagcagat gcagaatcca   1320
gacacactat cagccatgtc aaacccaaga gcaatgcagg ctttaatgca gatccagcag   1380
gggctacaga cattagccac tgaagcacct ggcctgattc cgagcttcac tccaggtgtg   1440
ggggtggggg tgctgggaac cgctataggc cctgtaggcc cagtcacccc cataggcccc   1500
ataggcccta tagtcccttt taccccccata ggcccccattg ggcccatagg acccactggc   1560
cctgcagccc ccctggctc caccggctct ggtggcccca cggggcctac tgtgtccagc   1620
gctgcaccta gtgaaaccac gagtcctaca tcagaatctg gacccaacca gcagttcatt   1680
cagcaaatgg tgcaggccct ggctggagca aatgctccac agctgccgaa tccagaagtc   1740
agatttcagc aacaactgga acagctcaac gcaatggggt tcttaaaccg tgaagcaaac   1800
ttgcaggccc taatagcaac aggaggcgac atcaatgcag ccattgaaag gctgctgggc   1860
tcccagccat cgtaa                                                    1875

<210> SEQ ID NO 3
<211> LENGTH: 21
<212> TYPE: DNA
<213> ORGANISM: Homo sapiens

<400> SEQUENCE: 3
tcccataaag agaccctaat a                                               21
```